(12) United States Patent
Mach et al.

(10) Patent No.: US 7,612,206 B2
(45) Date of Patent: Nov. 3, 2009

(54) SIGMA-2 RECEPTOR RADIOTRACERS FOR IMAGING THE PROLIFERATIVE STATUS OF SOLID TUMORS

(75) Inventors: Robert Mach, Eureka, MO (US); Michael J. Welch, Clayton, MO (US); Douglas J. Rowland, Davis, CA (US); Zhude Tu, Frontenac, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 12/044,952

(22) Filed: Mar. 8, 2008

(65) Prior Publication Data

US 2009/0041663 A1    Feb. 12, 2009

Related U.S. Application Data

(62) Division of application No. 10/903,771, filed on Jul. 30, 2004, now Pat. No. 7,390,902.

(60) Provisional application No. 60/491,582, filed on Jul. 31, 2003.

(51) Int. Cl.
*C07D 491/00*   (2006.01)
*A61K 51/00*    (2006.01)
*A61M 36/14*    (2006.01)

(52) U.S. Cl. .......................... 546/86; 546/87; 424/1.85; 424/1.81

(58) Field of Classification Search ................... 546/86, 546/87; 424/1.85, 1.81
See application file for complete search history.

(56) References Cited

U.S. PATENT DOCUMENTS

| | | | |
|---|---|---|---|
| 6,046,210 | A | 4/2000 | Stemp |
| 6,113,877 | A | 9/2000 | Mach |
| 6,447,748 | B1 | 9/2002 | John |
| 7,390,902 | B2 * | 6/2008 | Mach et al. ................. 546/86 |
| 2005/0107398 | A1 | 5/2005 | Mach et al. |
| 2008/0161343 | A1 | 7/2008 | Mach et al. |

FOREIGN PATENT DOCUMENTS

WO    2005048810    6/2005

OTHER PUBLICATIONS

International Search Report in the related application PCT/US08/655555 issued on Mar. 3, 2009.
International Search Report—PCT/U504/25304—Jun. 27, 2005.
Al-Nabulsi I, et al, Effect of ploidy, recruitment, environmental factors, and tamoxifen treatment on the expression of sigma-2 receptors in proliferating and quiescent tumour cells, Br. J. Cancer, 1999, p. 925-33, vol. 81(6).
Anderson CJ and Welch MJ, Radiometal-labeled agents (non-technetium) for diagnostic imaging, Chem. Rev., 1999, p. 2219-34, vol. 99(9).
Berardi F, et al, 4-(tetralin-1-yl)- and 4-(naphthalen-1-yl)alkyl derivatives of 1-cyclohexylpiperazine as sigma receptor ligands with agonist sigma2 activity, J. Med. Chem., 2004, p. 2308-17, vol. 47(9).
Bonhaus DW, et al., [3H]BIMU-1, a 5-hydroxytryptamine3 receptor ligand in NG-108 cells, selectively labels sigma-2 binding sites in guinea pig hippocampus, J. Pharmacol. Exp. Ther., 1993, p. 961-70, vol. 267(2).
Bowen WD, et al, CB-64D and CB-184: ligands with high sigma 2 receptor affinity and subtype selectivity, Eur. J. Pharmacol., 1995, p. 257-60, vol. 278(3).
Colabufo NA, et al, Distribution of sigma receptors in EMT-6 cells: preliminary biological evaluation of PB167 and potential for in-vivo PET, J. Pharm. Pharmacol., 2005, p. 1453-9, vol. 57(11).
Hou CT, et al, Characterization of a novel iodinated sigma-2 receptor ligand as a cell proliferation marker, Nucl. Med. Biol., 2006, p. 203-9, vol. 33(2).
Huang Y, et al, Synthesis and structure-activity relationships of naphthamides as dopamine D3 receptor ligands, J. Med. Chem., 2001, p. 1815-26, vol. 44(11).
Jurisson SS and Lydon JD, Potential technetium small molecule radiopharmaceuticals, Chem. Rev., 1999, p. 2205-18, vol. 99(9).
Kassiou M, et al, Synthesis and in vivo evaluation of a new PET radioligand for studying sigma-2 receptors, Bioorg. Med. Chem., 2005, p. 3623-6, vol. 13(11).
Mach RH, et al, Sigma 2 receptors as potential biomarkers of proliferation in breast cancer, Cancer Res., 1997, p. 156-61, vol. 57(1).
Mach RH, et al, Synthesis of 2-(5-bromo-2,3-dimethoxyphenyl)-5-(aminomethyl)-1H-pyrrole analogues and their binding affinities for dopamine D2, D3, and D4 receptors, Bioorg. Med. Chem., 2003, p. 225-33, vol. 11(2).
Mach RH, et al, Conformationally-flexible benzamide analogues as dopamine D3 and sigma 2 receptor ligands, Bioorg. Med. Chem. Lett., 2004, p. 195-202, vol. 14(1).
Tu Z, et al, Carbon-11 labeled sigma2 receptor ligands for imaging breast cancer, Nucl. Med. Biol., 2005, p. 423-30, vol. 35(5).

(Continued)

*Primary Examiner*—D. Margaret Seaman
*Assistant Examiner*—Nizal S Chandrakumar
(74) *Attorney, Agent, or Firm*—Sonnenschein, Nath and Rosenthal, LLP

(57) ABSTRACT

Novel benzamide compounds of Formula (I), Formula (II), and Formula (III), salts, water soluble salts, analogs and radiolabeled counterparts thereof as sigma-2 receptor radiotracers for imaging the proliferative status of solid tumors. A method for diagnosing a mammal for the presence of a mammalian tumor therein comprises administering to the mammal a diagnostic imaging detectable effective amount of a benzamide compound having a structure illustrated in Formula (I), Formula (II) and Formula (III) and detecting binding of the compound to a tumor in the mammal. A method for diagnostic imaging of a mammalian tissue having cell surface sigma-2 receptors comprising administering to a mammal a diagnostic imaging amount of a compound having a structure illustrated in Formula (I) Formula (II) and Formula (III) and detecting an image of a tissue having an ample cells with sigma-2 receptors.

39 Claims, 14 Drawing Sheets

OTHER PUBLICATIONS

Wheeler KT, et al, Sigma-2 receptors as a biomarker of proliferation in solid tumours, Br. J. Cancer, 2000, p. 1223-32, vol. 82(6).

Xu J, et al, [3H]N-[4-(3,4-dihydro-6,7-dimethoxyisoquinolin-2(1H)-yl)butyl]-2-methoxy-5-methylbenzamide: a novel sigma-2 receptor probe, Eur. J. Pharmacol., 2005, p. 8-17, vol. 525(1-3).

Supplementary Partial European Search Report issued on Oct. 10, 2008, in related application 04817745.5.

Curtet et al, New arylpiperazine derivatives as antagonists of the human cloned 5-HT4 receptor isoforms, J Med Chem, 2000, 43:3761-3769.

Hackling et al, N-(omega-(4-(2-methoxyphenyl)piperazin-1-yl)alkyl)carboxamides as dopamine D2 and D3 receptor ligands, J Med Chem, 2003, 46:3883-3899.

Leopoldo et al, Structure-affinity relationship study on N-[4-(4-arylpiperazin-1-yl)butyl]aryl carboxamides as potent and selective dopamine D3 receptor ligands, J Med Chem, 2002, 45:5727-5735.

* cited by examiner

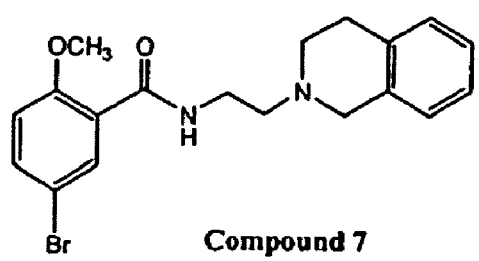
Compound 7
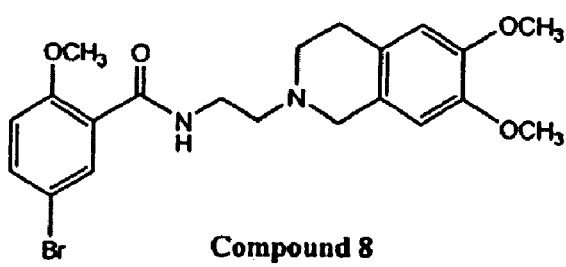
Compound 8
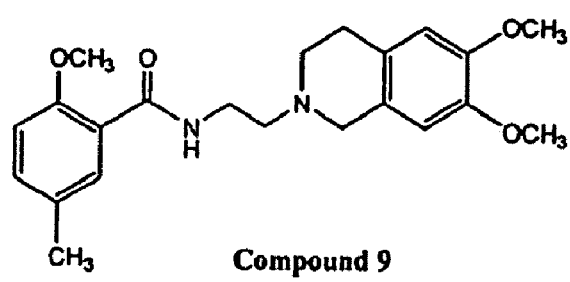
Compound 9
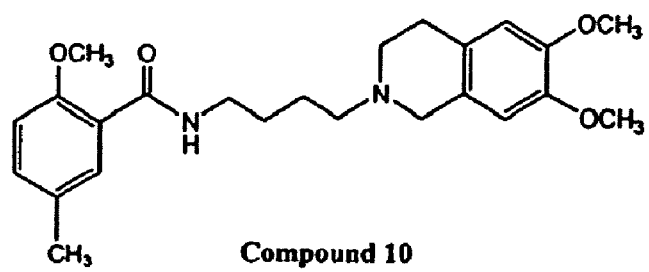
Compound 10
Figure 2

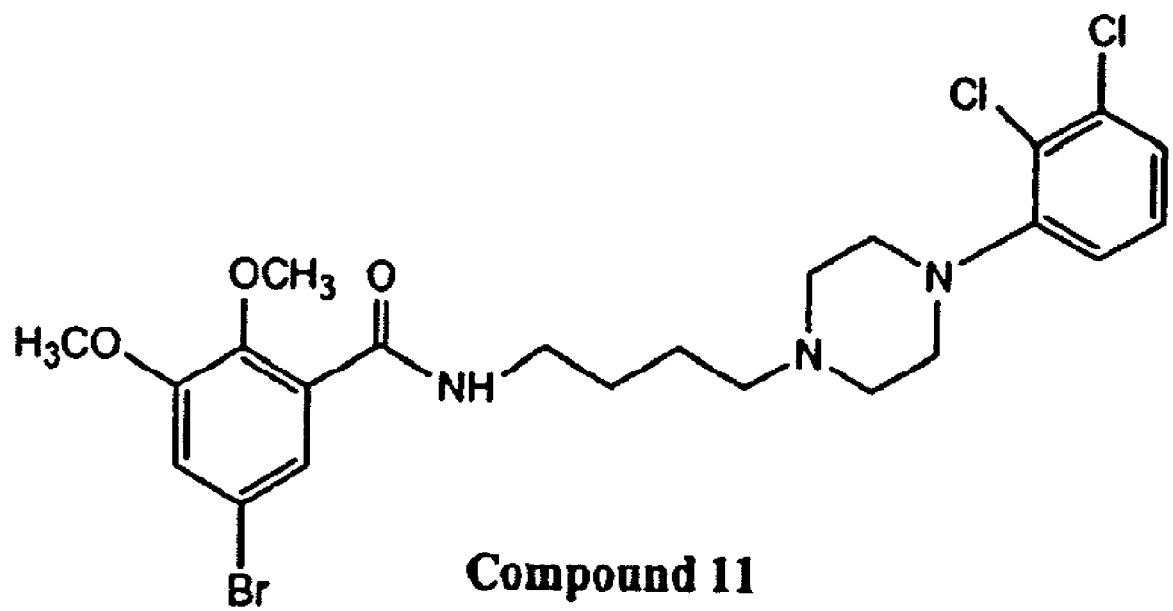
Compound 11
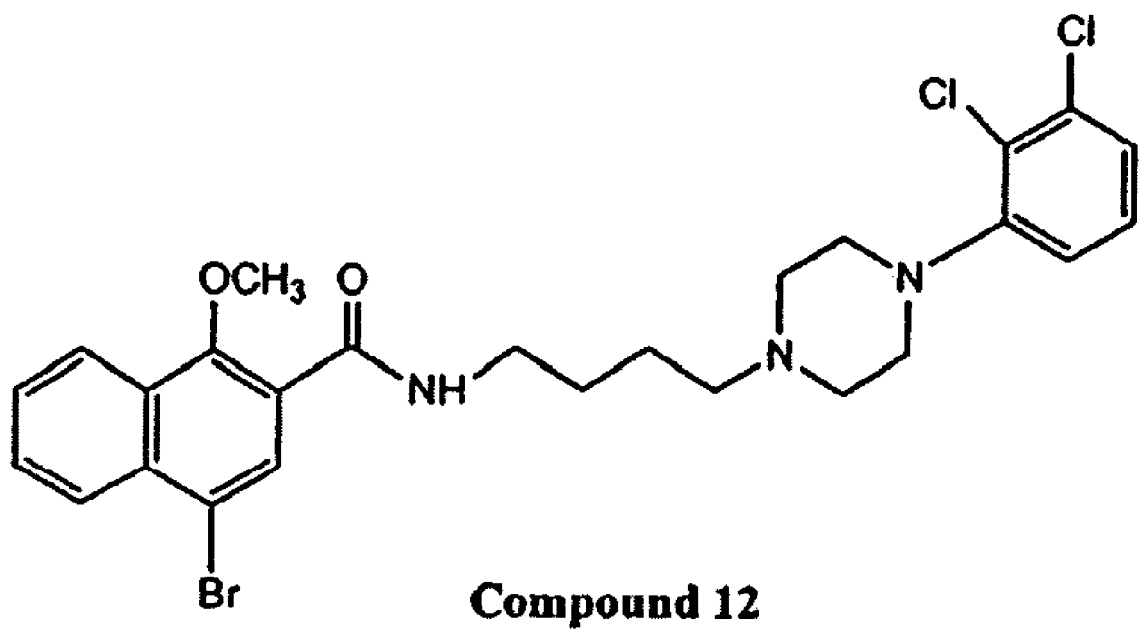
Compound 12
Figure 3

Figure 4. (a) BrCH$_2$CN or BrCH$_2$CH$_2$CH$_2$CN/Et$_3$N/CH$_2$Cl$_2$/RT; (b) LiAlH$_4$/THF or H$_2$/Pd(c)/ethanol; (c) Ref 10; (d) Ref 12.

Figure 5. (a) SOCl₂/benzene/reflux; (b) 19/Et₃N/CH₂Cl₂/RT; (c) 21/Et₃N/CH₂Cl₂/RT; (d) 22/CH₂Cl₂/Et₃N/RT.

Figure 6. (a) BrCH$_2$CH$_2$CH$_2$CN/Et$_3$N/CH$_2$Cl$_2$; (b) H$_2$/Pd(c)/ethanol; (c) Figure 5.

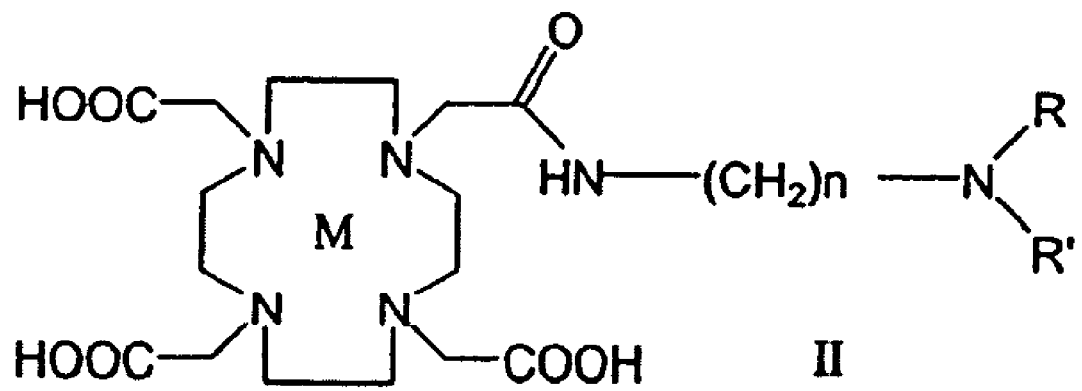
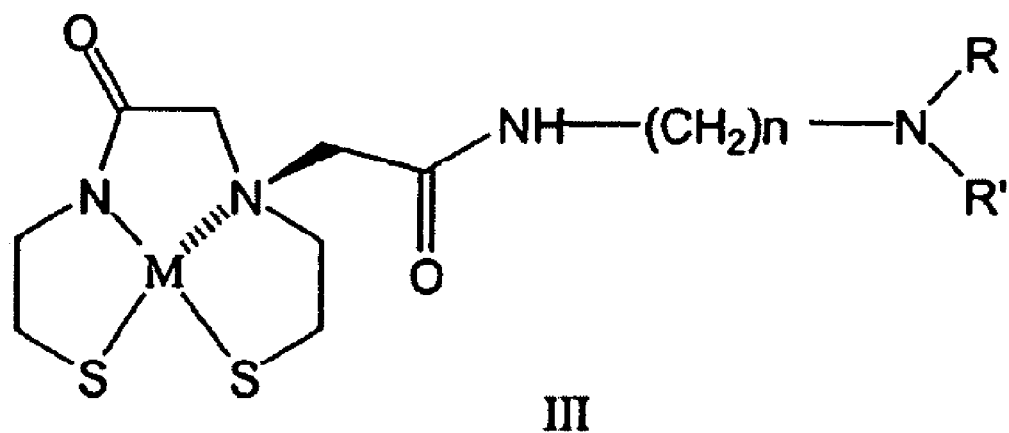
Figure 7.

Table IA. Binding Affinities for Dopamine $D_2/D_3$ and Sigma $\sigma_1/\sigma_2$ Receptors

| | $K_i (nM)^a$ | | | |
|---|---|---|---|---|
| # | $D_2^b$ | $D_3^c$ | $\sigma_1^d$ | $\sigma_2^e$ |
| 1 | 429.7 ± 76.1 | 17.8 ± 0.5 | 276.5 ± 35.7 | 716.5 ± 9.8 |
| 2 | 714.0 ± 133.7 | 21.4 ± 2.3 | 2,932 ± 28 | 16.4 ± 2.0 |
| 3 | 131.6 ± 24.6 | 81.6 ± 21.28 | 15.1 ± 1.7 | 47.7 ± 2.5 |
| 4 | 240.5 ± 19.4 | 126.5 ± 42.4 | 189.1 ± 2.6 | 21.2 ± 0.1 |
| 5 | 741.0 ± 287.3 | 106.5 ± 24.3 | 1,159 ± 7 | 17.6 ± 0.7 |
| 6 | 2,200 ± 390 | 627 ± 244 | 12,900 ± 111 | 8.2 ± 1.4 |
| 7 | 2,190 ± 351 | 310.7 ± 54.4 | 21.8 ± 5.6 | 89.4 ± 13.9 |
| 8 | 3,570 ± 796 | 488.0 ± 70.7 | 5,484 ± 266 | 12.4 ± 1.8 |
| 9 | 2,850 ± 316 | 3,760 ± 618 | 10,412 ± 462 | 13.3 ± 0.1 |
| 10 | 642.0 ± 141.0 | 313.0 ± 141.0 | 3,078 ± 87 | 10.3 ± 1.5 |
| 11 | 58.8 ± 13.7 | 2.1 ± 0.4 | 809 ± 66 | 75.0 ± 4.1 |
| 12 | 107.0 ± 19.0 | 10.2 ± 5.3 | 751 ± 6 | 26.4 ± 1.4 |
| 23 | N/A | N/A | 330.17±24.5 | 6.95±1.63 |

$^a$ MEAN ± SEM. $K_i$ VALUES WERE DETERMINED

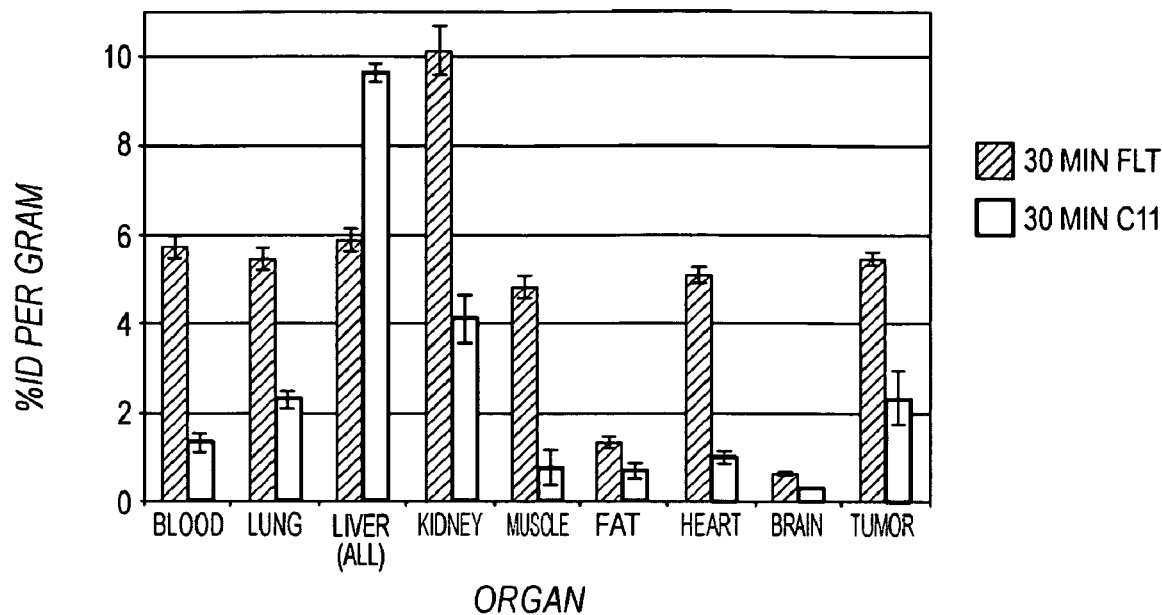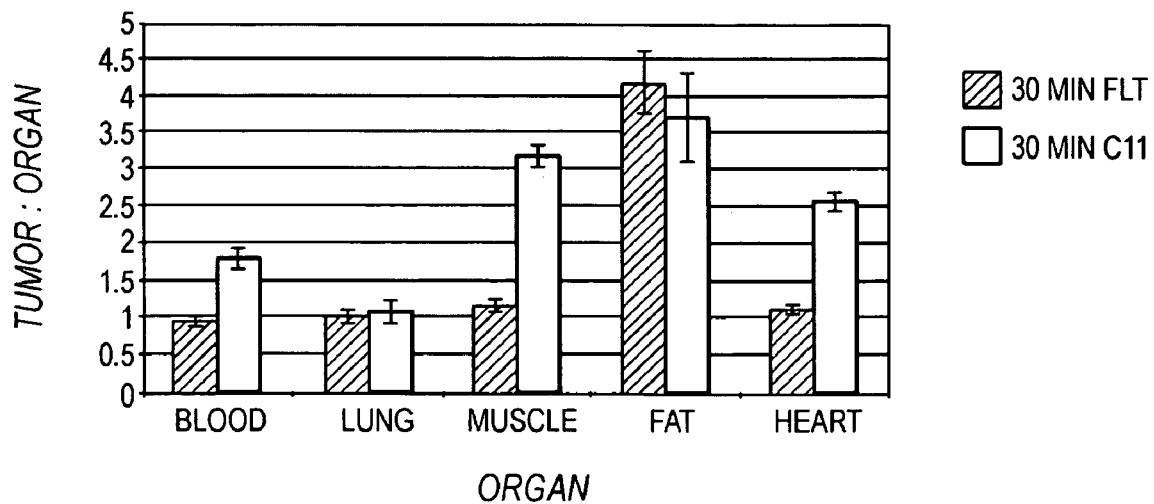
FIG. 9

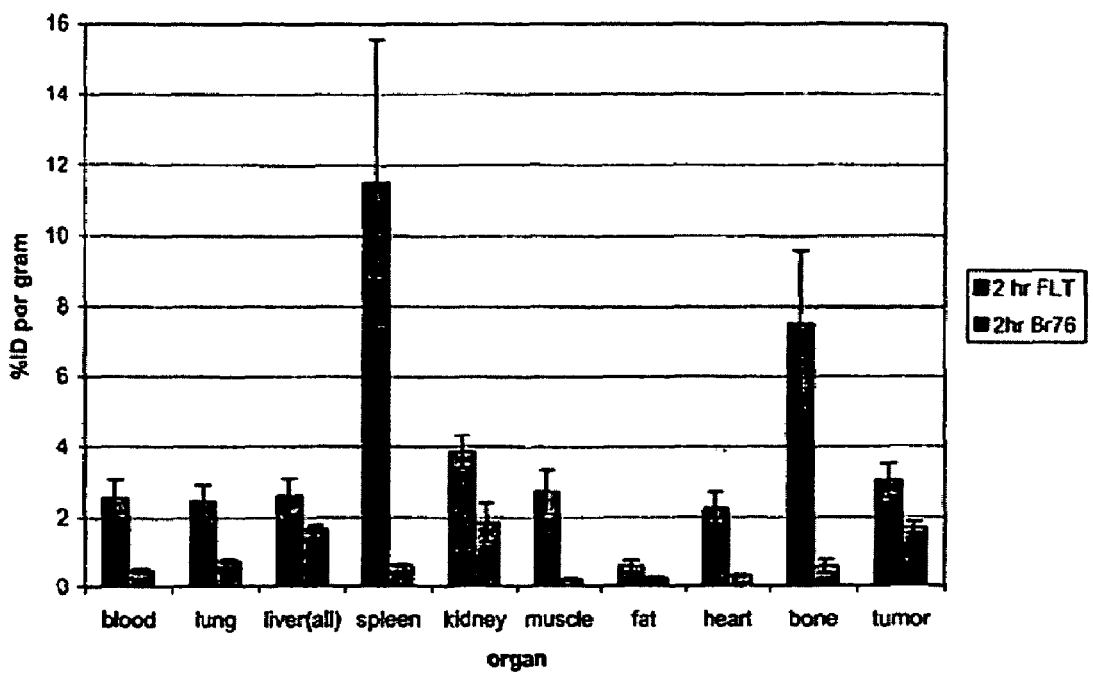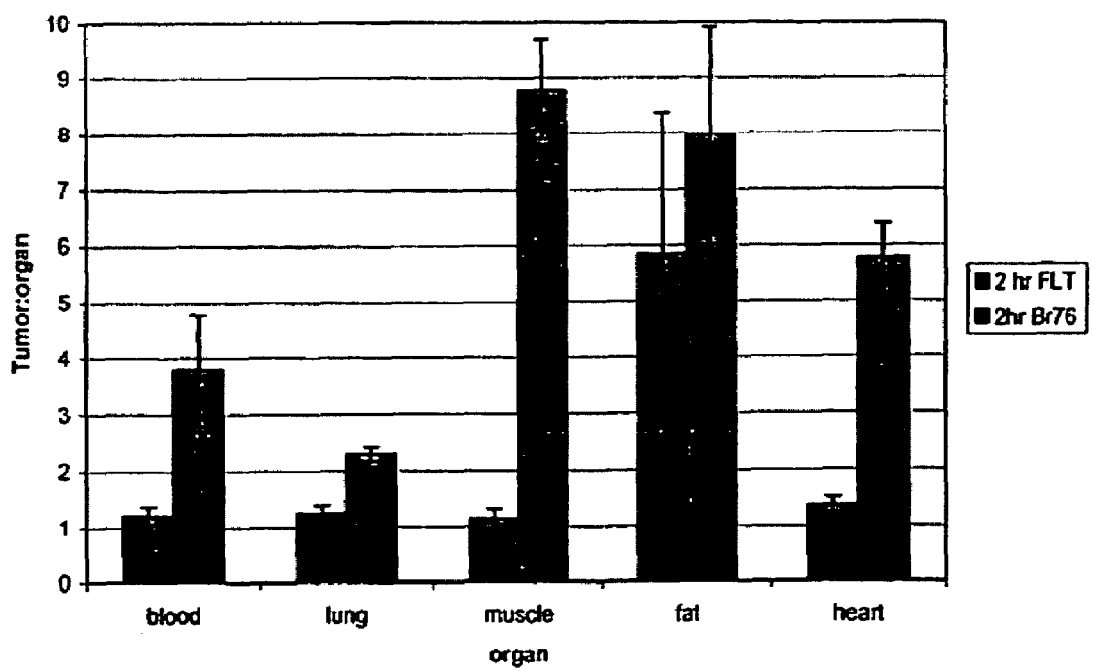
Figure 10 Comparison of [$^{18}$F]FLT with [$^{76}$Br]6 at 2 hrs post-i.v. injection. Notice the higher tumor:background ratios of [$^{76}$Br]6 versus that of [$^{18}$F]FLT.

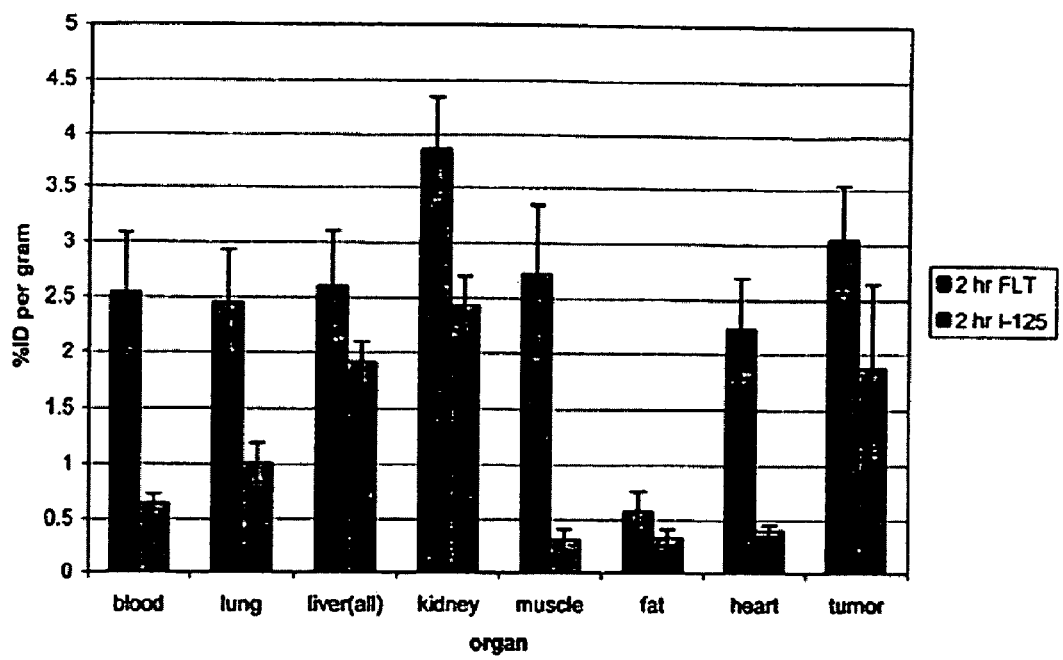
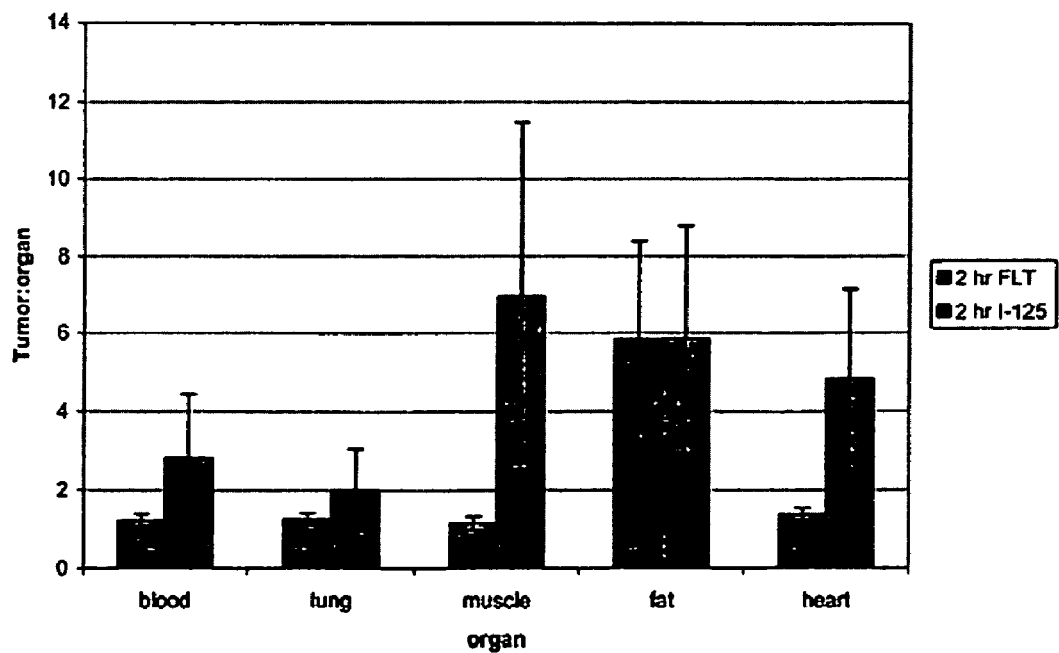
Figure 11. Comparison of [$^{18}$F]FLT with [$^{125}$I]6i at 2 hrs post-i.v. injection. Notice the higher tumor:blood, tumor:muscle, and tumor:heart ratios of [$^{125}$I]6i versus that of [$^{18}$F]FLT

SIGMA-2 RECEPTOR RADIOTRACERS FOR IMAGING THE PROLIFERATIVE STATUS OF SOLID TUMORS This application is a divisional of U.S. patent application Ser. No. 10/903,771 filed Jul. 30, 2004 now U.S. Pat. No. 7,390,902, and claims the benefit of U.S. Provisional Patent Application Ser. No. 60/491,582, filed Jul. 31, 2003. These applications are incorporated herein in their entirety by reference.

STATEMENT REGARDING FEDERALLY SPONSORED RESEARCH AND DEVELOPMENT

This invention was made with government support under grants DA 12647, CA86307 and CA102869 awarded by the National Institutes of Health and grant DAMD17-01-1-0446 awarded by the Department of Defense Breast Cancer Research Program of the US Army Medical Research and Material Command Office. The Government has certain rights in the invention.

FIELD OF THE INVENTION

This discovery relates to benzamide compositions comprising benzamide compounds, salts and analogs. This invention also relates to the use of benzamide compositions and benzamide compounds to prepare radiolabeled benzamide and to its uses in medicine and as a research tool.

BACKGROUND OF THE INVENTION

Cancer (malignant neoplasm) is the number two killer of people in the US. Each year in the U.S. more than a million people are diagnosed with cancer and half of those will ultimately die from the disease. Cancer also afflicts many other living mammals.

Cancer occurs when normal living mammalian cells undergo neoplastic (malignant) transformation. Cancer is tenacious in its ability to uncontrollably metastasize throughout the mammalian body thus giving rise to a high mortality rate in many situations, particularly breast cancer.

Breast cancer is characterized by a high proliferative potential that can vary considerably from patient to patient. No vaccine or other universally successful method for the prevention or treatment of breast cancer is currently available. The rate of tumor cell proliferation has been shown in breast tumors to predict the response to radiation therapy and chemotherapy. Presently, measures of tumor cell proliferation are obtained by histological or flow-cytometric analysis. Both methods are limited by sampling procedures and unfortunately only about 60% to about 70% of patient samples are suitable for flow cytometric analysis.

It has been demonstrated that sigma-2 ($\sigma_2$) receptors are expressed in high density in a number of human and rodent breast cancer cell lines (Cancer Research, 55, 408 (1995)). However, their expression in such cell lines is heterogenous, and their function is unknown.

Sigma ($\sigma$) receptors have also been identified as a distinct class of receptors that are expressed in liver, kidneys, endocrine glands, and in the central nervous system. Apart from the normal expression of sigma receptors in these tissues, several studies have reported their over expression in human and murine tumors (1-3). It has also been shown that there are two types of this receptor, $\sigma_1$ and $\sigma_2$ receptors. The $\sigma_2$ receptor has been demonstrated to be a reliable biomarker for the proliferative status of solid tumors (2-4). Up regulation of $\sigma_2$ receptors during proliferation was shown by selectively recruiting cells into quiescent and proliferative states and then measuring the receptor concentration (2-4). It was found that $\sigma_2$ receptor concentrations increased tenfold when cells were recruited to proliferative states. Therefore, radioligands are desired that have both high affinity and high selectivity for $\sigma_2$ receptors as tracers for the non-invasive assessment of the proliferative status of human solid tumors using noninvasive diagnostic imaging procedures such as PET and SPECT. To this end, a high affinity and highly selective $\sigma_2$ radioligand is needed for the assessment of tumor status.

One of the major problems in the clinical management of breast cancer is the early detection and identification of an appropriate treatment strategy. A complication that has limited successful treatment is the inability to assess the proliferative status of breast tumors since breast cancer has a malignant potential that can vary considerably from patient to patient. The use of surrogate markers of proliferation such as the presence or absence of tumors in axillary lymph nodes suffers from a low sensitivity and specificity. Other methods such as determining the S-phase fraction of tumor biopsy or fine needle aspirates suffers from sampling problems associated with tumor heterogeneity that may not provide a true representation of the proliferative status of a solid tumor.

A recent strategy has focused on using noninvasive imaging procedures such as Positron Emission Tomography (PET) in order to assess the proliferative status of an entire tumor. This approach has relied primarily on the development of agents that target the increase in metabolic activity (i.e., [$^{18}$F]FDG) or increased DNA (DNA precursors such as [$^{11}$C]thymidine) or protein (i.e., [$^{11}$C]methionine) synthesis associated with tumor proliferation. However, the majority of these agents have proven to be inadequate for providing an accurate measure of the proliferative status of solid tumors for a variety of reasons.

Cancer cure rates have increased dramatically over the years. This trend as a result of the widespread use of improved screening procedures that often lead to the early diagnosis/detection of cancer. However, as more selective treatment strategies have been developed, it is necessary to develop new and improved diagnostic procedures that can be used earlier to determine a potential treatment strategy based on the biological properties and proliferation of the tumor. In addition, it is desired to develop and have available non-invasive procedures that can provide the means for determining either a positive or negative response to a treatment strategy as early as possible thus extending the mammalian host's viability.

Additionally a continuing need exists for enhanced non-invasive methods that can accurately assess the proliferative status of breast cancer, as such methods could have a significant positive impact on determining an optimal therapy for treating human breast cancer patients.

BRIEF DESCRIPTION OF THE INVENTION

In an aspect, the discovery comprises a benzamide composition comprising benzamide compound(s), salts, analogs and radiolabeled counterparts thereof, having at least one structure or substantially similar structure of at least one of the structures illustratively depicted hereinafter in one or more of Formula (I), Formula (II) and Formula (III), analogs and salts thereof and their respective radioactive labeled counterparts of such benzamide compounds, salts and their analogs having use as a radioimaging agent(s).

In an aspect benzamide compositions including benzamide compounds include those compounds having a structure shown in the structure in Formula (I):

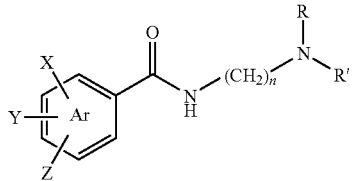
(I)

where Ar symbolically represents a substitutable chemical moiety comprising one of either a substitutable aromatic ring or a substitutable heteroaromatic ring; X, Y, Z represents a moiety substitutable on Ar and selected from the group consisting of H (hydrogen), halogen (I, Br, Cl, F), $C_1$-$C_4$ alkoxy, $C_1$-$C_4$ alkyl, $C_1$-$C_4$ fluoroalkyl, $C_1$-$C_4$ fluoroalkoxy, $CF_3$, $OCF_3$, $SCH_3$, $SCF_3$, $NH_2$; n is an integer independently ranging from 2 to about 10 such as 2, 3, 4, 5, 6, 7, 8, 9, 10; and NRR' is at least one of (a):

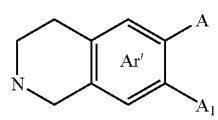
(a)

wherein A and A1 each symbolically represent chemical moieties independently substitutable on Ar' selected from the group consisting of independently H, alkyl ($C_1$-$C_4$) or $C_1$-$C_4$ alkoxy or one of

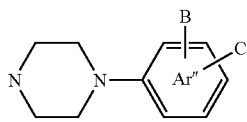
(b)

wherein B and C each symbolically represent independent substitutable chemical moieties independently selected from the group consisting of H, halogen (I, Br, Cl, F), $C_1$-$C_4$ alkoxy, alkyl ($C_1$-$C_4$), $C_1$-$C_4$ fluoroalkyl, $C_1$-$C_4$ fluoroalkoxy, $CF_3$, $OCF_3$, $SCH_3$, $SCF_3$ and $NH_2$, and R and $R_1$ are two independently selected conjoined and/or linked cyclic aromatic organic moieties, n is an integer the same or different as N in (a) above and N herein, independently varies from 1 to ten such as 1, 2, 3, 4, 5, 6, 7, 8, 9 and 10 and wherein Ar, Ar', Ar" are independently selected substitutable aromatic rings and their respective radioactive labeled counterparts and compound 13 and compound 14.

In an aspect, compounds 1, 2, 3, 4, 5, 6, 7, 8, 9, 10, 11, 12 and 23 of Formula (I) and compound 13 of Formula (II) and compound 14 of Formula (III) are depicted respectively structurally as:

Compound 1
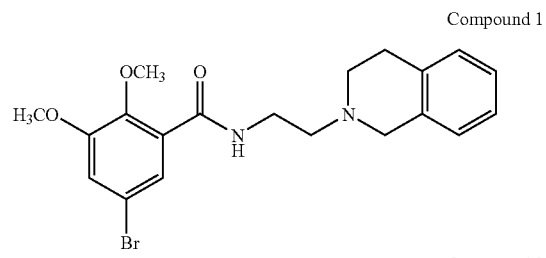

Compound 2
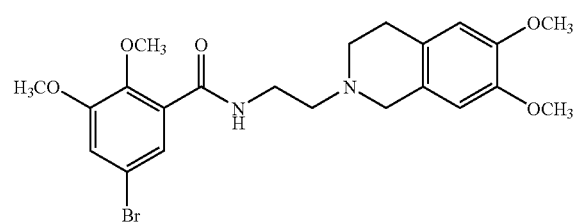

Compound 3
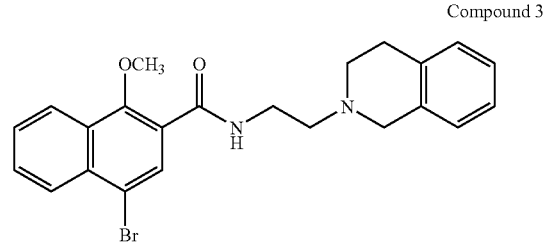

Compound 4
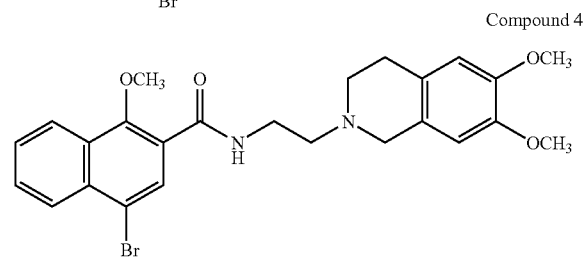

Compound 5
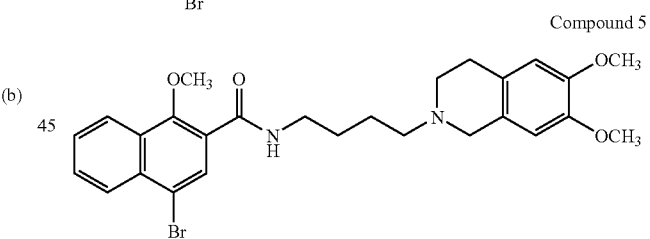

Compound 6
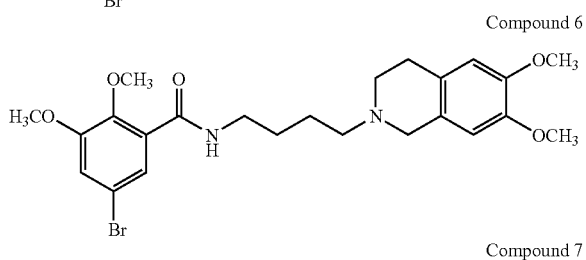

Compound 7
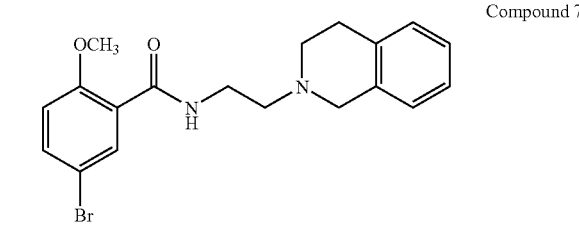

-continued

Compound 8
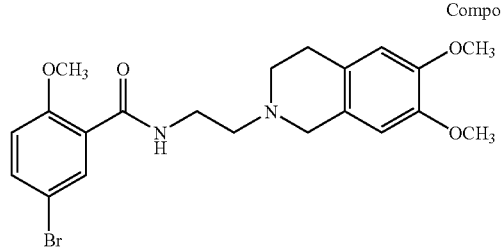

Compound 9
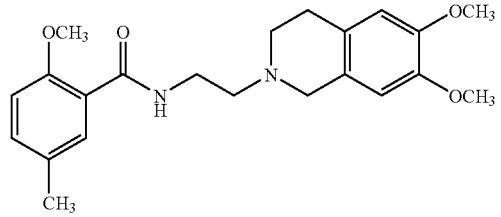

Compound 10
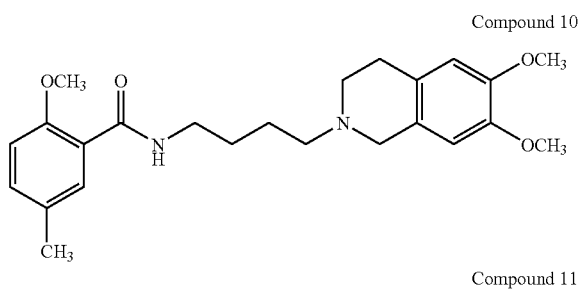

Compound 11
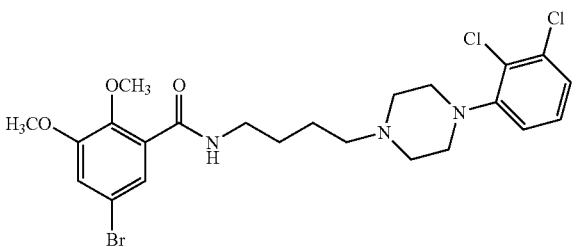

Compound 12
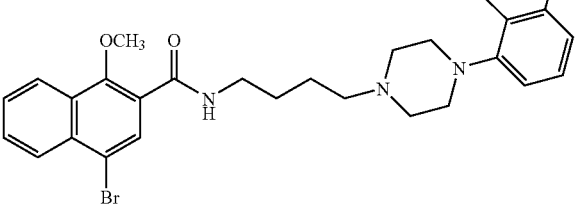

Including compound 23 and

Compound 13
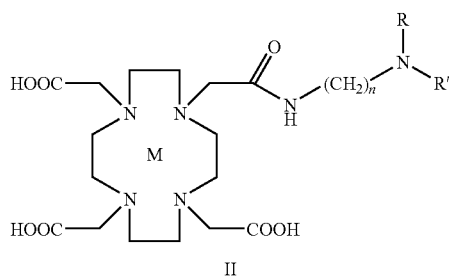

II

-continued

Compound 14
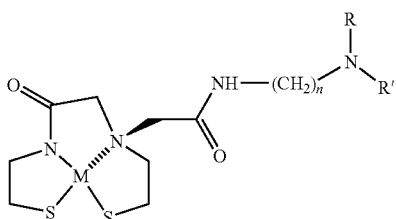

III and (the) respective radiolabeled counterparts of compounds 1, 2, 3, 4, 5, 6, 7, 8, 9, 10, 11 and 12, 13, 14 and 23.

In an aspect, a benzamide composition comprises a benzamide compound further comprises compound 6 labeled with at least one of $^{76}$Br, $^{123}$I, $^{124}$I and $^{125}$I. In an aspect, the compound is compound 10 labeled with ($^{11}$C).

In an aspect, the novel compound 6 comprises $^{76}$Br.

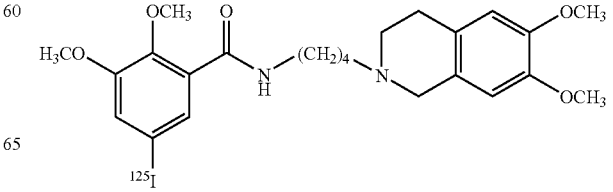

In an aspect, the novel compound 6i comprises $^{123}$I.

In an aspect, the novel compound 6i comprises $^{124}$I.

In an aspect, the novel compound 6i comprises $^{125}$I.

In an aspect, the novel compound 10 comprises $^{11}C$.

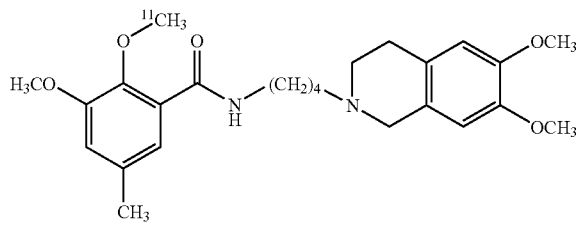

In an aspect, a process for the preparation of a compound selected from one of compounds 1, 2, 3, 4, 5, 6 depicted structurally in FIG. 4 comprises respectively reacting a compound

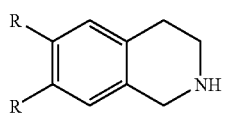

(a)

having a formula wherein R is hydrogen or methoxy with a compound of the formula

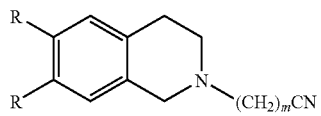

wherein R in this structural depiction is a substitutable moiety selected from hydrogen or methoxy and independently m is an integer from one to 3 with bromoacetonitrile or bromobutyronitrile to produce an N-alkylated product

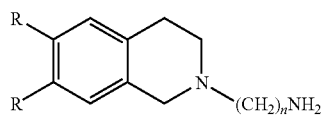

wherein when R is hydrogen, n is an integer independently 2-4 and wherein R is independently methoxy then n is an integer 2-4 and (b) reducing the N-alkylated product with lithium aluminum hydride in THF or hydrogenating the N-alkylated compound over palladium on charcoal to provide an intermediate amine product depicted structurally as compound 19, 20, 21 and 22 in FIG. 4, and (c) condensing the intermediate amine product with either 2-methoxy-5-bromonaphtholy chloride or 5-bromo-2,3-dimethoxybenzoic acid to produce a compound having as its structure a structure selected from one structures shown for compounds 1-6.

In an aspect, a process for the preparation of a compound 7, 8, 9 and 10 structurally depicted FIG. 5 comprises reacting a compound of the formula

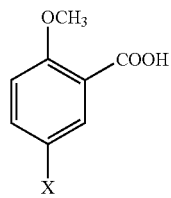

wherein X is a substitutable moiety independently halogen or alkyl $C_1$-$C_8$ with thionyl chloride and one of butyronitrile or bromobutyronitrile to produce compound of 7, 8, 9 and 10 of FIG. 5. In an aspect X comprises bromide. In an aspect X comprises methyl.

In an aspect, a process for the preparation of a compound having a structure depicted as 11 and/or 12 comprises:

(a) reacting a compound having a structure of the formula

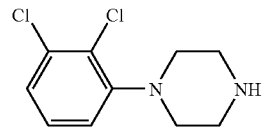

(b) with bromoacetonitrile to produce a compound having the structure shown in the formula

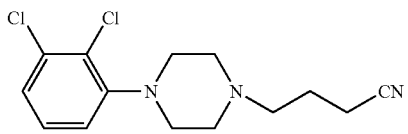

(b) hydrogenating that compound over palladium on charcoal to prepare a compound of the structural formula

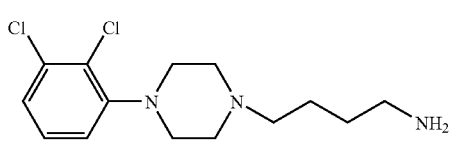

(c) and condensing that compound with either of 2-methoxy-5-bromonaphthoyl chloride or 5-bromo-2,3-dimethoxybenzoic acid respectively to produce compound (II) and compound (12) respectively.

In an aspect, a process for the preparation of a compound having a structure depicted as compound 23, which comprises reacting the corresponding phenol with 1-bromo-2-fluoroethane.

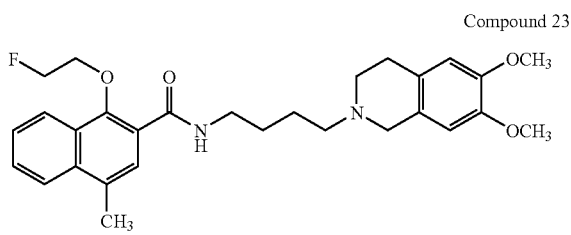

Compound 23

Compound 23 is depicted in Formula I. Compound 23 is useful in all aspects diagnostic, treatment, medicinal and research tool use aspects of this discovery.

In an aspect, a non-invasive method for diagnosing a mammal for the presence of a cancer comprises administering to the mammal a diagnostic imaging detectable effective amount of a benzamide composition comprising a benzamide detectably radio labeled compound having a structure selected from at least one of the benzamide compounds illustratively depicted in Formula (I), compound 13 depicted in Formula (II) and compound 14 depicted in Formula (III) and detecting binding of the at least one benzamide compound in the mammal. In an aspect the method comprises determining that a mammalian tumor is present in the mammal upon detecting binding, thus diagnosing the mammal. In an aspect the method further comprises producing an acquisition of the detection.

In an aspect, a marker for cancer comprises a detectably-labeled benzamide composition comprising a benzamide compound having a structure of at least one of the structures illustratively depicted of benzamide compounds illustratively depicted in Formula (I), compound 13 depicted in Formula (II) and compound 14 depicted in Formula (III) and having an explicit provocative binding efficacy to a tumor in a living mammal. In an aspect the detectably labeled benzamide compound is a highly selective $\sigma_2$ radioligand having the aforementioned structure effectively and functionally appended with a radioactive ligand.

In an aspect, a novel pharmaceutical composition comprises a benzamide composition comprising a benzamide compound having as a structure at least one of structures shown for novel benzamide compounds illustratively depicted in Formula (I) compound 13 depicted in Formula (II) and compound 14 depicted in Formula (III) and a pharmaceutically (pharmacologically) acceptable diluent or carrier. In an aspect a pharmaceutical composition comprises a detectably labeled benzamide compound having a structure illustratively depicted in one of the compounds 1-12 and 23 illustratively depicted in Formula (I), compound 13 depicted in Formula (II) and compound 14 depicted in Formula (III) and a pharmaceutically acceptable diluent or carrier. In an aspect the detectably labeled benzamide compound is a highly selective $\sigma_2$ radioligand having the aforementioned structure appended with a radioactive ligand.

In an aspect, a pharmaceutical composition effective for treating human or non-human neoplastic disorder comprises a detectably labeled pharmaceutically effective amount of at least one compound having a structure of at least one of the structures illustratively depicted in one of the benzamide compounds illustratively depicted in Formula (I), compound 13 depicted in Formula (II) and compound 14 depicted in Formula (III) in a composition including a pharmaceutically acceptable carrier. In an aspect the detectably labeled benzamide compound is a highly selective $\sigma_2$ radioligand having the aforementioned benzamide structure appended with a radioactive ligand.

In an aspect, a non-invasive method to determine the proliferative status of a cancer cell in a living mammal comprises administering to a living mammal afflicted with a solid malignant tumor, an effective amount of a detectably labeled benzamide composition comprising a benzamide compound having a structure of at least one of the benzamide compounds 12 illustratively depicted in Formula (I) compound 13 depicted in Formula (I) and compound 14 depicted in Formula (III) and determining the extent to which the detectably labeled benzamide compound binds to cells of a tumor in the mammal, the extent providing a measure of the proliferative status of the cancer cells. In an aspect the living mammal is a human. In an aspect, determining the proliferative status includes assessing the proliferative status of a breast cancerous tumor.

In an aspect, a method for pharmacologically treating a mammalian tumor as a disorder in a mammal comprises administering to a mammal having a tumor a composition including a tumor-inhibiting amount of at least one detectably-labeled benzamide compound having a structure of the structure shown of at least one of the benzamide compounds illustratively depicted in Formula (I), compound 13 depicted in Formula (II) and compound 14 depicted in Formula (III) In an aspect the mammal is a living human.

In an aspect, a non-invasive method for diagnostic imaging of a mammalian tissue having ample cell surface sigma-2 receptors comprises administering to the tissue of the mammal a diagnostic imaging amount of at least one compound having a structure of at least one of the detectably labeled benzamide compounds illustratively depicted in Formula (I), compound 13 depicted in Formula (II) and compound 14 depicted in Formula (III) and detecting an image of a tissue having an ample cells with sigma-2 receptors. In an aspect the mammal is a human. In an aspect, the image is used to diagnose living mammalian tissue.

In an aspect a non-invasive method for in vitro detection of a cancer cell in living mammalian tissue sample comprises contacting a mammalian tissue sample comprising a cell with an in vitro diagnostic imaging amount of at least one detectably radiolabeled benzamide composition comprising a benzamide compound having a structure of at least one of the benzamide compounds illustratively depicted in Formula (I), compound 13 depicted in Formula (II) and compound 14 depicted in Formula (II) for a time and under conditions sufficient and effective for binding of the compound to the cell and detecting such binding indicative of an association with the present of cancer. In an aspect the mammal is a living human. In an aspect the detecting is by image acquisition.

In an aspect, the cell(s) is in a previously obtained representative biological sample from a mammal. In an aspect, the novel compounds herein, including the radiolabeled counterparts are useful in the treatment of cancer.

In an aspect, a non-invasive method for in vitro detection of a cancer cell in a living mammalian tissue sample comprises contacting a mammalian tissue sample with an in vitro diagnostic imaging detectable and acquisitionable amount of at least one detectably radiolabeled benzamide composition/compound having as a structure a structure of at least one of the benzamide compounds illustratively depicted in Formula (I), compound 13 depicted in Formula (II) and compound 14 depicted in Formula (III) for a time and under cellular conditions functionally sufficient and effective for binding of the compound to the cancer cell and detecting such binding. In an aspect such binding is indicative of the presence of a cancer cell. In an aspect the mammal is a human.

In an aspect, a method for determining proliferation and/or progression of a cancer as a disorder in a living mammal comprises administering to a living mammal a diagnostic imaging detectable amount of at least one detectably radiolabeled benzamide composition comprising a benzamide compound having as a structure a structure of at least one of the benzamide compounds illustratively structurally depicted in Formula (I), compound 13 depicted in Formula (II) and compound 14 depicted in Formula (III) at a first selected time, detecting an image of a tissue having ample cells with sigma-2 receptors at a second selected (later) time respectively detecting an image of a tissue having ample cells with sigma-2 receptors at both times, comparing the images and determining if the detected image at the later time is smaller than the detected image at the first time. In an aspect the elapsed time between the first time and second time is selected to be a time duration significant amount. In an aspect the mammal is a living human. In an aspect the comparison is used to determine proliferation and/or progression of a cancer in a mammal.

In an aspect, a non-invasive method for identifying a modulating effect (and regression effect) of a cancer in a living mammal with a disorder, comprises administering to the mammal a diagnostic imaging detectable amount of at least one detectably radiolabeled benzamide composition comprising a benzamide compound and having a structure of at least one of the structures illustrated in Formula (I), Formula (II) and Formula (III) at a first time, detecting and acquisitioning an image of a tissue having ample available cells with sigma-2 receptors, administering a detectably-labeled benzamide compound having a structure of at least one of the compound structures illustrated in Formula (I) including compound 23, Formula (II) and Formula (III) to the mammal and at a second (later) time respectively detecting and acquisitioning an image of a tissue having an abundance of cells with sigma receptors, comparing the respective images and determining that there has been an prophylactic effect and/or regression and/or modulation. In an aspect the comparison shows the amount of regression over time. In an aspect the mammal is a living human. In an aspect the comparison shows the prophylactic effect of the compound and its toxicity to cancer. In an aspect the comparison shows the efficacy of the compound towards killing cancer in a living mammal. In an aspect the detectably-labeled benzamide compound is tagged with a radioactive ligand.

In an aspect, a non-invasive method for diagnosing and determining the response of a mammalian patient(s) with a disorder to tailored drug therapy comprises administering to a mammal a diagnostic imaging detectable amount of at least one detectably labeled benzamide compound having a structure of at least one of the benzamide compounds illustratively depicted in Formula (I) including compound 23, compound 13 depicted in Formula (II) and compound 14 depicted in Formula (III) at a first and second (later) times respectively, detecting an image of a tissue having an abundance of cells with sigma receptors at both times, comparing the images and determining/diagnosing if the image at a later time is larger than the image at the first time that there has been a proliferative effect or progression of cancer. In an aspect the dynamic comparison shows the proliferation and progression of the cancer over elapsed time. In an aspect the mammal is a living human. In an aspect a method for diagnosis and determining the response is a determination of a prophylaxis or management of a disorder associated with neoplastic cells.

In an aspect, a non-invasive method of screening candidate chemicals for toxicity/lethality to cancer comprises administering to a mammal a diagnostic imaging detectable amount of at least one detectably labeled benzamide compound selected from the benzamide compounds illustratively depicted in Formula (I) including compound 23, compound 13 depicted in Formula (II) and compound 14 depicted in Formula (III) at a first or initial time, detecting and acquisitioning an image of a tissue having ample cells with sigma-2 receptors, administering to the mammal a candidate chemical, detecting and acquisitioning an image of tissue having ample cells with sigma-2 receptors at a secure time subsequent the first time, comparing the detected images and making a determination as to whether there has been a proliferative effect and progression of the cancer. In an aspect the mammal is a human. In an aspect the chemicals are organic or inorganic.

In another aspect, a non-invasive medical treatment for a mammal and a method of medically treating a mammal comprises administering to a mammal a diagnostic imaging detectable amount of at least one detectably labeled benzamide compound having a structure of at least one of the benzamide compounds illustratively depicted in Formula (I) including compound 23, compound 13 depicted in Formula (II) and compound 14 depicted in Formula (III) at a first and second (later) time respectively, detecting an image of a tissue having ample cells with sigma receptors at a first time and a second time, the second time subsequent the first time comparing the images taken respectively and determining if the image at the later time is larger than the image at the first time that there has been a proliferative effect and progression of the cancer. In an aspect the mammal is a human. In an aspect the treatment is a cancer treatment. In an aspect medical treatment includes a method of retarding, preventing, and ameliorating disease or a medical affliction in a mammal.

In an aspect, a non-invasive method of customizing drug therapy for a living mammalian subject comprises effectively and capably administering to the subject, the mammal undergoing drug therapy, a diagnostic imaging detectable amount of at least one radiolabeled benzamide compound having a structure of at least one of the benzamide compounds illustratively depicted in Formula (I) including compound 23, compound 13 depicted in Formula (II) and compound 14 depicted in Formula (III), detecting an image of a tumor having ample capably radionuclide detectable sigma-2 receptors and making a determination regarding a drug therapy based on the captured images. In an aspect, the determination comprises an adjuvant therapy to the drug therapy.

BRIEF DESCRIPTION OF THE FIGURES

FIG. 2 illustratively shows structured depictions of novel conformationally flexible benzamide compounds 7, 8, 9 and 10 of Formula (I).

FIG. 3 illustratively shows structured depictions of novel conformationally flexible benzamide compounds 11 and 12 of Formula (I).

FIG. 7 shows structured depictions of conformationally flexible benzamide compound (13) of Formula (II) and conformationally flexible benzamide compound (14) of Formula (III) respectively labeled with a metal chelating group comprising an emitting radionuclide "(M)".

Table IA shows structures and in vitro binding data.

Figure 8:
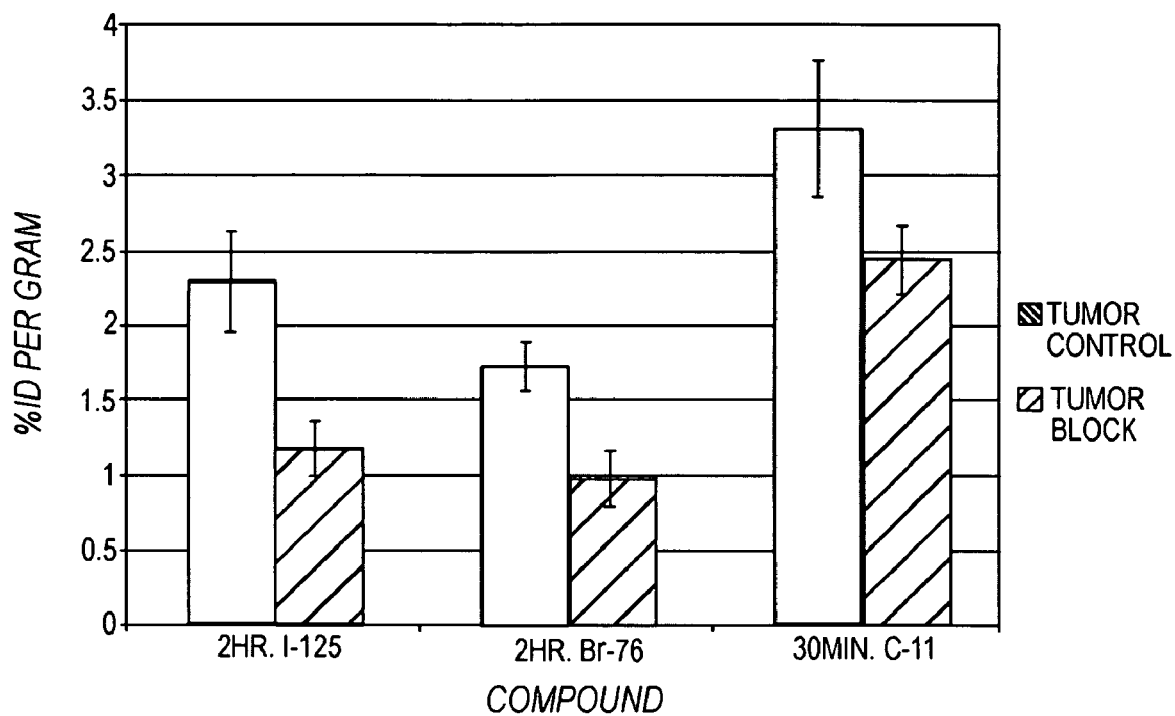

FIG. 8 shows in vivo blocking studies of [$^{125}$I]6i (left), [$^{76}$Br]6 (center), and [$^{11}$C]10 (right) in tumor-bearing mice. The blocking agent was YUN 143, which has a high affinity for $\sigma_1$ and $\sigma_2$ receptors. Animals were sacrificed at the time point displaying the highest % I.D./gram tumor. The data are consistent with the labeling of $\sigma_2$ receptors in vivo by each radiotracer.

FIG. 9 shows a comparison of [$^{18}$F]FLT ((18)F-3'-fluoro-3'-deoxy-L-thymidine PET (FLT PET)) and [$^{11}$C]10. Although [$^{18}$F]FLT has a high uptake in tumors (top graph), the high uptake of radioactivity in normal tissues results in a lower tumor:background radio of [$^{18}$F]FLT relative to [$^{11}$C]10, particularly the tumor:muscle, tumor:blood, and tumor:heart ratios (bottom graph).

FIG. 10 shows a comparison of [$^{18}$F]FLT with [$^{76}$Br]6 at 2 hrs post-i.v. injection. Notice the higher tumor:background ratios of [$^{76}$Br]6 versus that of [$^{18}$F]FLT.

FIG. 11 shows a comparison of [$^{18}$F]FLT with [$^{125}$I]6i at 2 hrs post-i.v. injection. Notice the higher tumor:blood, tumor:muscle, and tumor:heart ratios of [$^{125}$I]6i versus that of [$^{18}$F]FLT.

Figure 12:
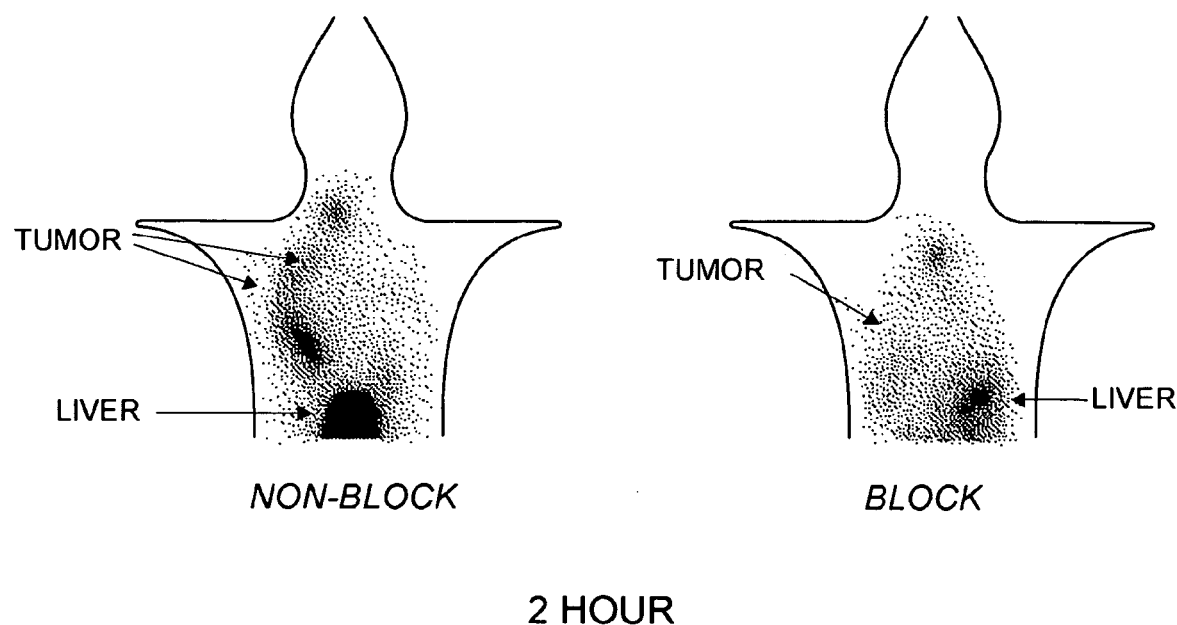

FIG. 12 shows MicroPET® imaging studies of [$^{76}$Br]6 in Balb-c mice bearing an EMT-6 breast tumor xenograft (EMT-6 BALB-C mice). The no-carrier-added (NCA) study is on the left and the sigma receptor blocking study (1 mg/kg, i.v. YUN-143) is shown on the right.

Figure 13:
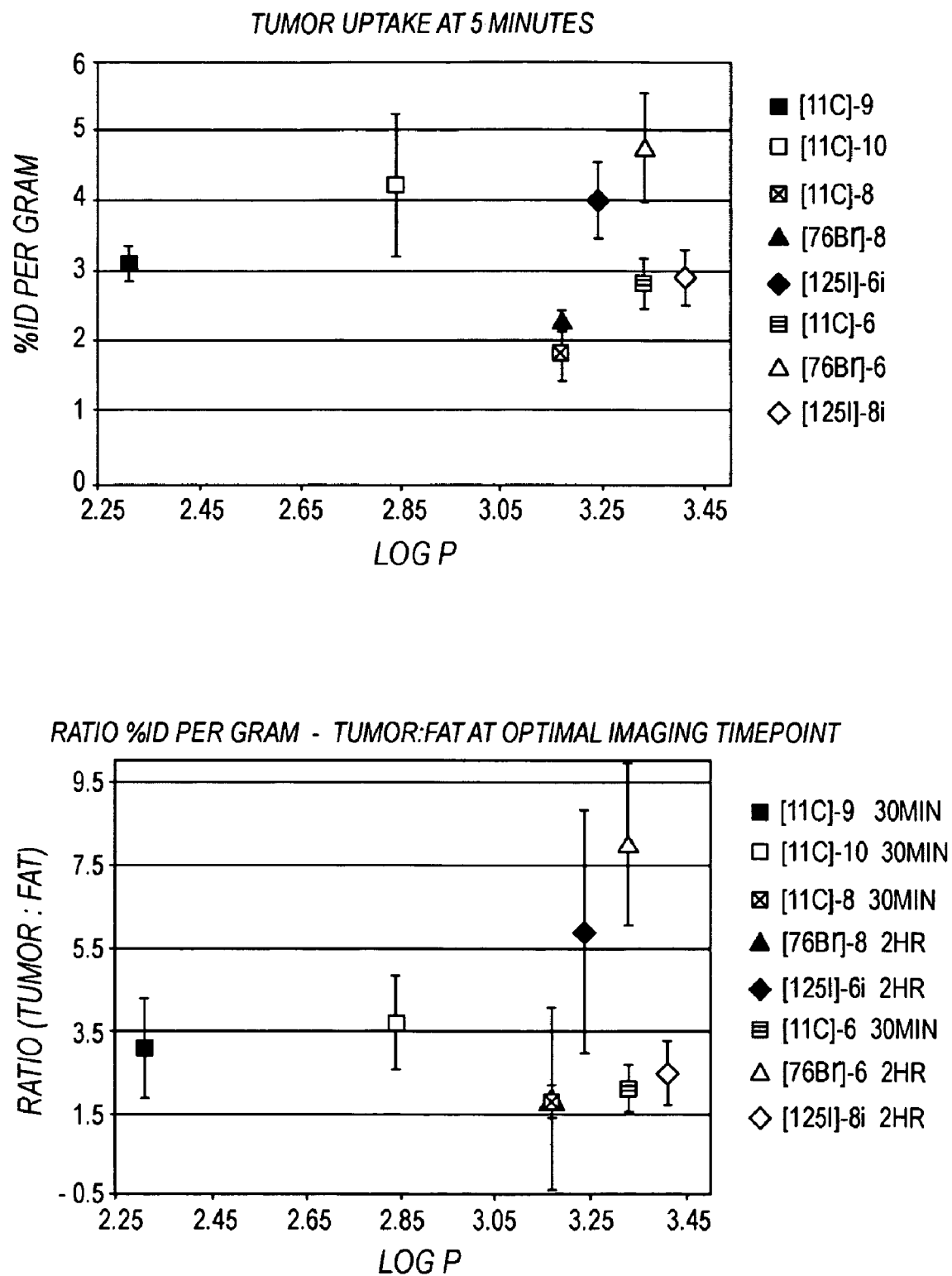

FIG. 13 shows graphs comparing the uptake of the benzamide analogs with % uptake in breast tumors at 5 min (top) and the tumor:fat ratio at the optimal imaging time (bottom). There was no correlation between tumor uptake or tumor:fat ratio and log P. Note that all compounds had a high tumor uptake at 5 min post-injection. The high tumor:fat ratio of [$^{76}$Br]6 and [$^{125}$I]6i was due to the later time point after injection used because of the longer half-life of Br-76 and I-125 versus that of C-11.

DETAILED DESCRIPTION OF THE INVENTION

The present discovery is understood more readily by reference to the following detailed description of the discovery and the Examples included therein.

As used herein the phrase "benzamide compound" illustratively depicted in Formula (I) including compound 23, compound 13 depicted in Formula (II) and compound 14 depicted in Formula (III) includes any moiety derived from or of the benzamide compound in any form including pharmaceutically effective and acceptable water soluble salt form, radical, analogs, ionic form, ion, conformational form, radiolabeled conformational form, radiolabeled ion and mammalian and metabolic derivatives thereof. Acceptable salts include but are not limited to tosylate, methanesulfonate, acetate, citrate, malonate, tartrate, succinate, benzoate, ascorbate, alpha-ketoglutarate, and alpha-glycerophosphate. Suitable inorganic salts include hydrochloride, sulfate, nitrate, bicarbonate, and carbonate salts.

This discovery relates to benzamide compounds having a specific affinity for sigma-2 receptors believed indicative of the presence of carcinoma(s) and melanoma(s) in a living mammal such as a human. Further this discovery relates to benzamide compositions as sigma-2 receptor radiotracers for imaging the proliferative status of solid tumors.

The invention relates to benzamide compounds and to their analogs and salts and to the use of benzamide compounds, salts and analogs thereof to prepare detectably radiolabeled benzamide compounds, including salts and analogs thereof which are useful in biological competitive assays to test for and detect the presence of sigma-2 receptors associated with cancer or pre-cancerous conditions. The discovery further relates to the use of benzamide compound(s) as radiolabeled benzamides including salts and analogs thereof which are useful in medicinal and diagnostic chemistry for detecting cancer in living mammals.

In an aspect, a benzamide compound is provided to a living mammal such as to a human by effective administration of an aqueous composition (such as a saline composition) comprising a salt of benzamide associated with an emitting radionuclide or a salt of an analog of benzamide with an associated (labeled) emitting radionuclide to the living mammal such as a human. In an aspect the salt is a water soluble salt. An adjuvant may be employed if desired in aqueous compositions of this invention.

As used herein, the term "radiolabeled counterparts" includes respective radiolabeled benzamide compounds which are also novel.

As used herein, the term "tumor:background ratio" (i.e., tumor:fat ratio, tumor:muscle ratio, tumor:lung ratio, tumor:blood ratio) refers to the % injected dose/g tissue of the radiotracer in the tumor divided by the % injected dose/g tumor in the background tissue (i.e., fat, muscle, lung, blood).

As used herein, the term "detectably labeled" includes the respective pharmacologically acceptable radiolabeled benzamide compounds having an effective amount of an emitting radiolabel therewith and suitably accepting an emitting radiolabel for use in administration to living mammals.

As used herein, the term "$^{76}$Br Compound 6" means a compound having a structure of that structure depicted in structure 6 radiolabeled with $^{76}$Br similarly schematically for $^{123}$I, $^{124}$I, $^{125}$I, and for $^{11}$C Compound 10.

In an aspect the term, "$C_1$-$C_4$" comprises at least one of methyl, ethyl, propyl, isopropyl, butyl, isobutyl and isobutyl.

In an aspect the term, "alkoxy $C_1$-$C_4$" comprises at least one of methoxy, ethoxy, propoxy and butoxy.

As used herein the term "fluoroalkyl" includes fluoro $C_1$ to $C_4$ and includes fluoromethyl, fluoroethyl, fluoropropyl and fluorobutyl.

As used herein the term "fluoroalkoxy" include fluoro $C_1$ to $C_4$ alkoxy and includes fluoromethoxy, fluoroethoxy, fluoropropoxy and fluorobutoxy.

As used herein, the term "salt" includes water soluble salt and includes alkali and alkaline earth metal salts including but not limited to sodium, potassium, magnesium and calcium.

As used herein, the term "alkyl" and "alkoxy" include substituted alkyl and substituted alkoxy.

As used herein, the symbol "I" means iodine, the symbol "Br" means bromine, the symbol "Cl" means chlorine, the symbol "F" means fluorine and the symbol "H" means hydrogen.

As used herein, the term "provocatively" means aggressively and actively and having a sufficient and effective reaction capability.

As used herein, the term "medicinal chemistry" means a chemistry-based medicinal practice involving one or more of the biological, medical and pharmaceutical sciences.

As used herein, the term "administration" includes the giving of a compound by any useful effective means to a living mammal and its successful introduction into the mammal such as in its gastrointestinal tract in an effective method which results in that compound, its salt, its ions, metabolites, analogs, radionuclides or derivatives being made biologically available to that mammal receiving administration of benzamide for medicinal use. In an aspect the mammal is a living human. In an aspect the living mammal is a nonhuman such as a canine or feline. In an aspect the benzamide compound is made biologically available to the gastro intestinal tract of the mammal patient.

As used herein, the expression "pharmaceutically or pharmacologically acceptable" includes a benzamide composition comprising a benzamide compound and its radiolabeled counterpart which contains composition ingredients that are compatible with other ingredients of the composition as well as physiologically acceptable to the recipient, e.g. a mammal such as a living human, without the resulting production of excessive undesirable and unacceptable physiological effects or a deleterious impact on the mammal being administered the pharmaceutical composition. In an aspect, a composition for use comprises one or more carriers, useful excipients and/or diluents.

As used herein, the term "dosage" includes that amount of novel benzamide compound which when effectively administered to a living mammal provides an effective amount of biologically available benzamide compound to the living mammal.

In an aspect, as used herein the term "patient" includes a human subject and a human individual. In an aspect the patient includes a human, and a non-human such as feline, canine, horse and murine.

Terminology used herein is for the purpose of describing particular aspects only and is not intended to be limiting in any regard.

It must be noted that, as used in the specification the singular forms "a," "an," and "the" include plural referents unless the context clearly dictates otherwise.

Figure 1:
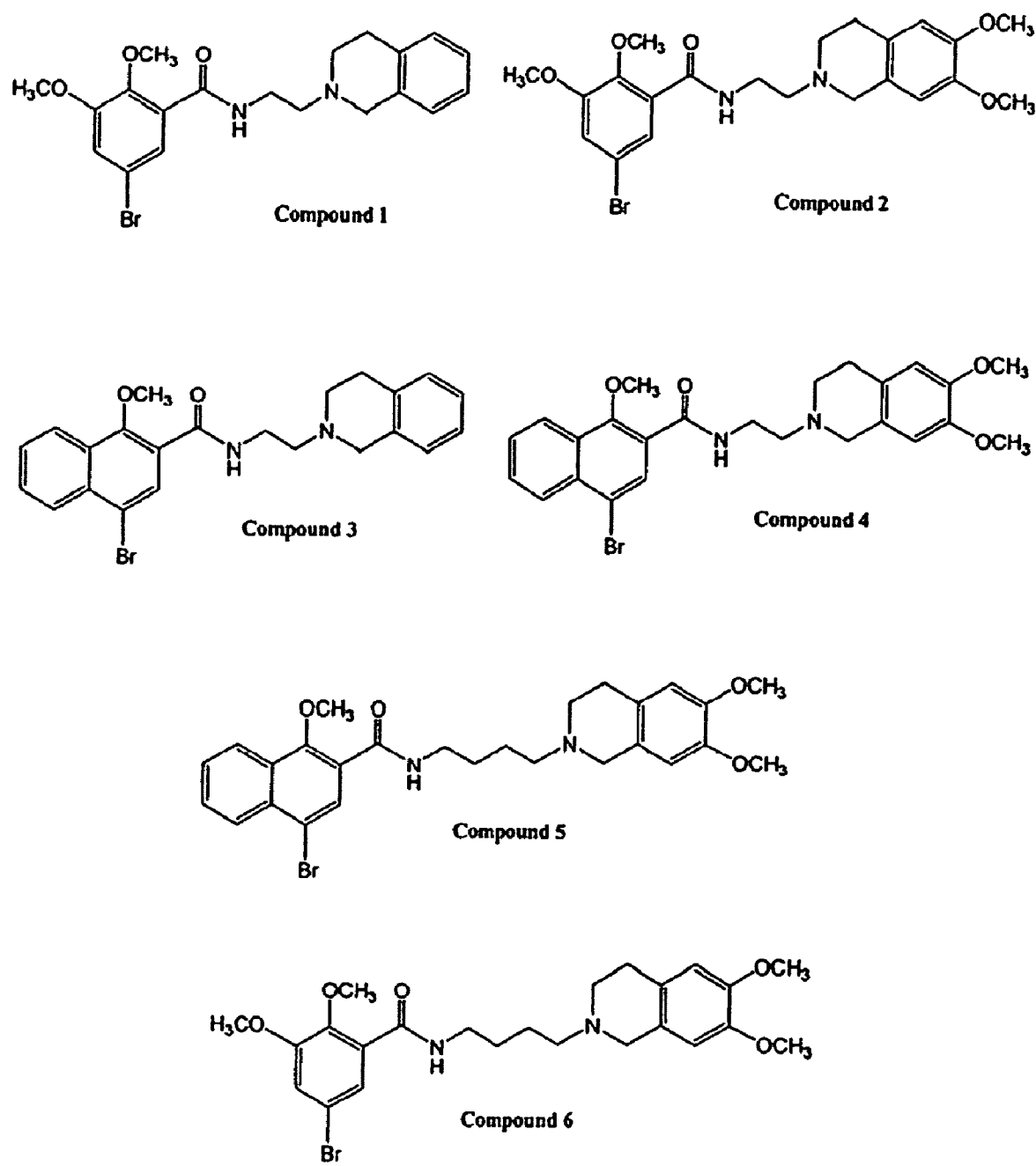
FIG. 1 illustratively shows structured depictions of novel conformationally flexible benzamide compounds 1, 2, 3, 4, 5 and 6 and compound 23 of Formula (I).

As used in the specification, claims and drawings, for convenience numbers 1-12 refer respectively to various structures of novel benzamide compounds of Formula (I) structurally depicted respectively in FIGS. 1, 2 and 3, Formula (II) and Formula (III) of FIG. 7.

The invention provides benzamide compounds of Formula (I), Formula (II) Formula (III) and medicinal methods using such compounds administered to patients for detecting and treating cancer including but not limited to cancers such as blastomas, gliomas, pheochromocytomas, melanomas, colon, renal, prostate, lung and breast carcinomas in living mammals.

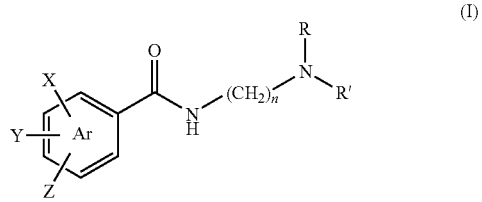

(I)

where Ar is a substitutable moiety comprising either a substitutable aromatic ring or substitutable heteroaromatic ring; X, Y, Z is a moiety selected from the group consisting of H, halogen (I, Br, Cl, F), $C_1$-$C_4$ alkoxy, alkyl ($C_1$-$C_4$), $C_1$-$C_4$ fluoroalkyl, $C_1$-$C_4$ fluoroalkoxy, $CF_3$, $OCF_3$, $SCH_3$, $SCF_3$, $NH_2$; n is an integer ranging from 2 to about 10; and NRR' is at least one of (a):

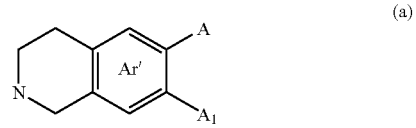

(a)

wherein A and A1 are each substitutable moieties selected from the group consisting of independently H, alkyl ($C_1$-$C_4$) or $C_1$-$C_4$ alkoxy or

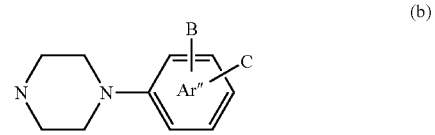

(b)

wherein B, C are each substitutable moieties independently selected from the group consisting of H, halogen (I, Br, Cl, F), $C_1$-$C_4$ alkoxy, $C_1$-$C_4$ alkyl, $C_1$-$C_4$ fluoroalkyl, $C_1$-$C_4$ fluoroalkoxy, $CF_3$, $OCF_3$, $SCH_3$, $SCF_3$ and $NH_2$ and R and R1 are two conjoined and linked cyclic aromatic organic moieties, n is an integer varying from 1 to ten such as 1, 2, 3, 4, 5, 6, 7, 8, 9 and 10 and wherein Ar, Ar', Ar" are independently individual multi-substitutable aromatic rings and their respective novel radiolabeled counterparts.

In an aspect, novel benzamide compounds comprise conformationally flexible benzamide compounds having a structure shown as one of structures 1, 2, 3, 4, 5 and 6 shown in FIG. 1; a structure such as a structure shown structures 7, 8, 9 and 10 in FIG. 2; a structure such one of structures 11 and 12 in FIG. 3 and structures 13 of Formula (II) and structure 14 of Formula (III) of FIG. 7. In an aspect, novel detectably-labeled benzamide compounds include such aforerecited novel benzamide compounds having radiolabels attached.

In an aspect, compounds 1-12 and 23 of Formula (I) are depicted structurally as:

Compound 1

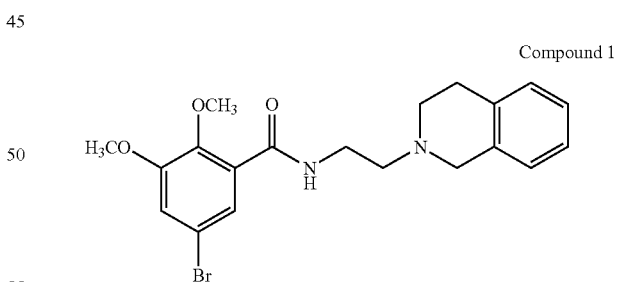

Compound 2

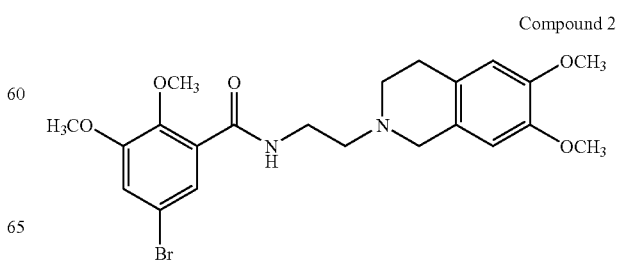

-continued

In a chemical aspect compounds 1, 2, 3, 4, 5, 6, and 23 are benzamide analogs. Compounds 7, 8, 9, and 10 are benzamides and compounds 11 and 12 are 2 and 3-dichlorophenylpiperazine benzamide and naphthamide analogs.

In an aspect the inventive compounds comprise conformationally flexible detectably-labeled benzamide compounds of Formula (I) including compound 23, Formula (II) and Formula (III) which provocatively bind to a cell surface sigma receptor and exhibit exquisite cell specificity and affinity for cancerous cells such as at least one of the aforerecited blastomas, gliomas, pheochromocytomas, melanomas, colon, renal, prostate, lung and breast carcinomas in living mammals and for cells having sigma-2 receptors.

The invention also compasses a process for the preparation of benzamide compounds and their radiolabeled counterparts, salts, analogs and pharmaceutical compositions thereof.

In an aspect a process for the preparation of a benzamide compound selected from compounds 1, 2, 3, 4, 5, 6 and 23 of Formula (I) comprises respectively:

(c) reacting a compound having a formula wherein R is

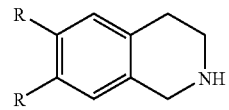

hydrogen or methoxy with a compound of the formula

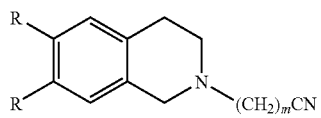

wherein R is an independently substitutable moiety selected from hydrogen or methoxy and m is an integer from one to 3 with bromoacetonitrile or bromobutyronitrile to produce an N-alkylated product

Figure 4:
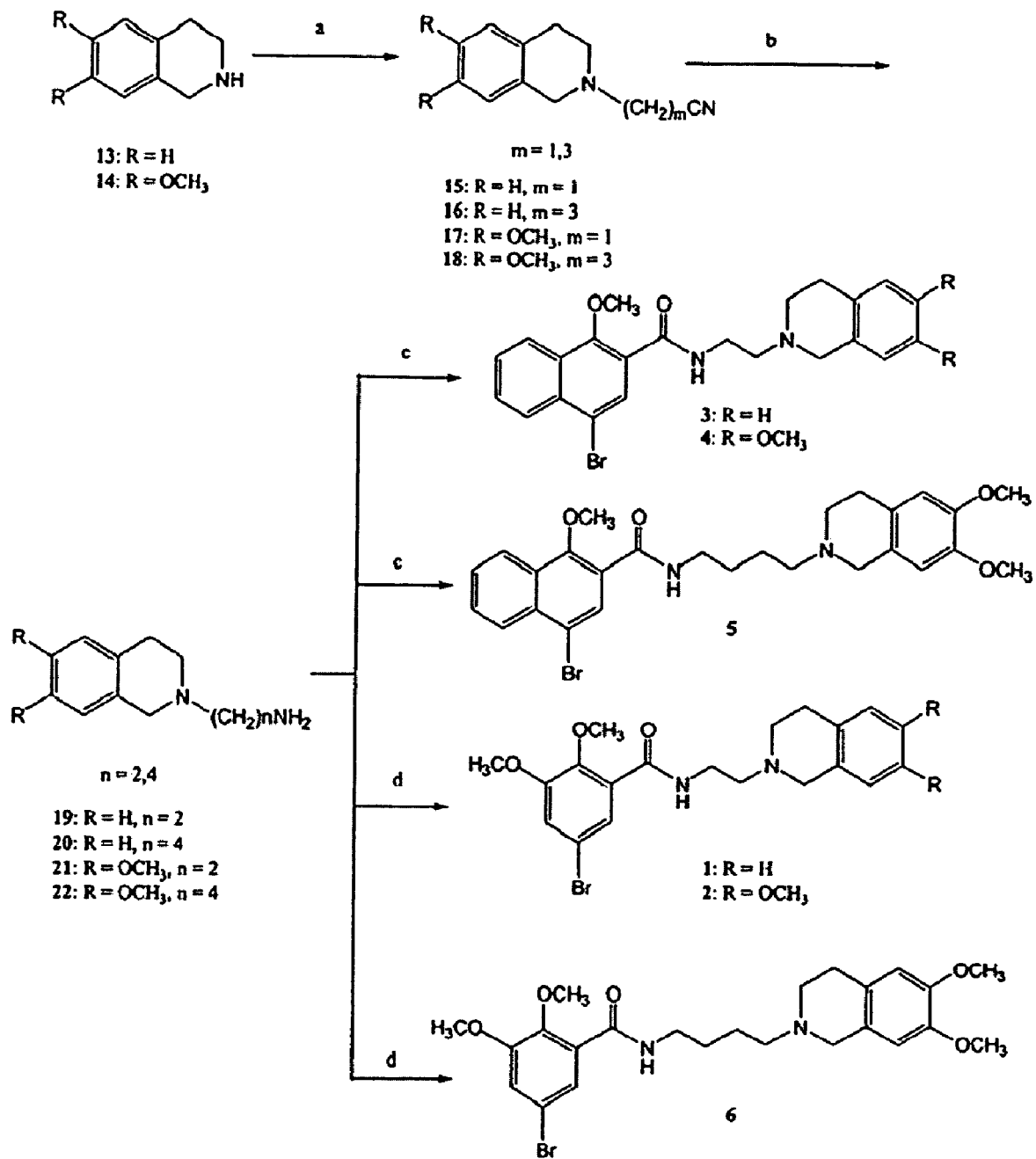
FIG. 4 shows an illustrative process for preparing novel conformationally flexible benzamide compounds (1, 2, 3, 4, 5 and 6) in 1 of Formula (I).

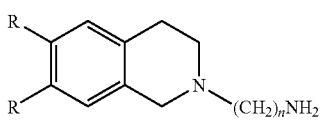

wherein when R is hydrogen, n is integer identity 2-4 and wherein R is methoxy and n is an integer ranging from 2-4 and (b) reducing said N-alkylated product with either lithium aluminum hydride in (THF) or hydrogenating said N-alkylated compound over palladium on charcoal to provide an intermediate amine product denoted as compound 19, 20, 21 and 22 on FIG. 4, and c) condensing said amine product with either 2-methoxy-5-bromonaphtholy chloride or 5-bromo-2,3-dimethoxybenzoic acid to produce a compound selected from one of compounds 1, 2, 3, 4, 5 and 6.

In an aspect a process for the preparation of compound depicted as 7, 8, 9 and 10 of Formula (I) comprises reacting a compound of the formula

Figure 5:
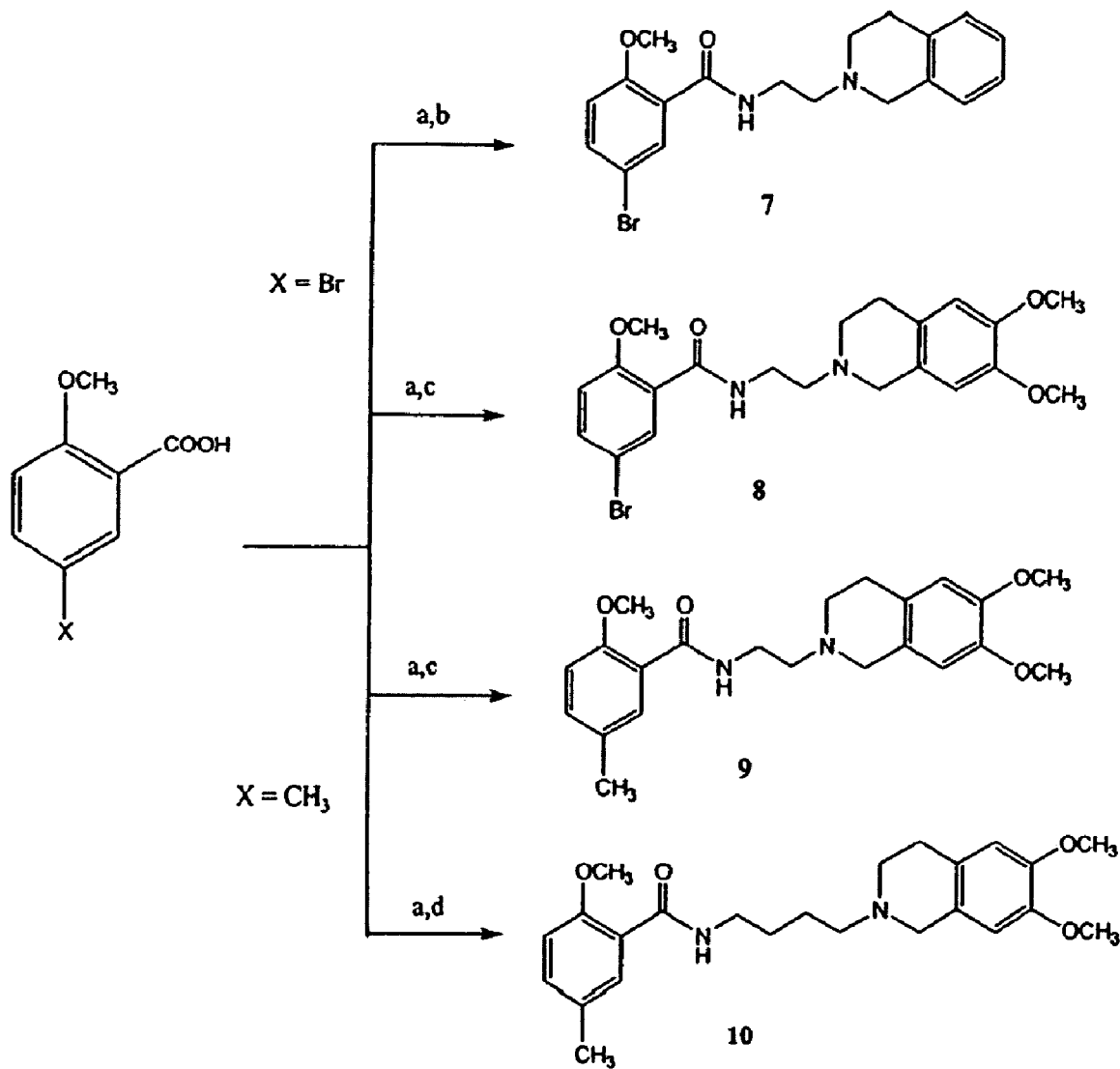
FIG. 5 shows an illustrative process for preparing novel conformationally flexible benzamide compounds (7, 8, 9, and 10) of Formula (I).

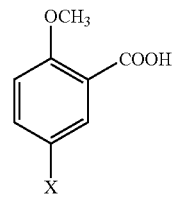

wherein X is a substitutable halogen or alkyl $C_1$-$C_8$ with thionyl chloride and one of butyronitrile or bromobutyronitrile to respectively produce compound 7, 8, 9 and 10 depicted structurally FIG. 5. In an aspect X comprises bromide. In an aspect X comprises methyl.

In an aspect a process for the preparation of a compound(s) denoted as 11 and 12 respectively of Formula (III) comprises:

(a) reacting a compound having a structure of the formula depicted as

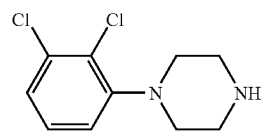

with bromoacetonitrile to produce a compound of the formula

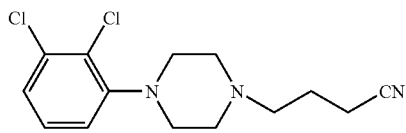

(b) hydrogenating that compound over palladium on charcoal to provide a compound of the formula

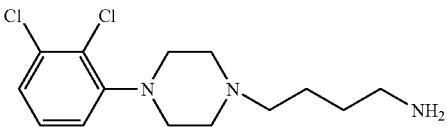

and condensing that compound with either of 2-methoxy-5-bromonaphth-oyl chloride or 5-bromo-2,3-dimethoxybenzoic acid to provide compound 11 and compound 12.

In an aspect reaction conditions are employed which provide for the effective reaction of the reaction processes disclosed herein. In an aspect effective reaction time and reaction conditions are provided so as to allow preparation of the desired intermediates and final products of the reactions.

More in particular the invention relates to the use of one or more of a detectably-radiolabeled benzamide compound(s) of Formula (I), Formula (II) and Formula (III) and their pharmaceutically acceptable salts for non-invasive diagnostic imaging of living mammalian tissue having cells expressing sigma-2 receptors.

The present invention provides detectably radiolabeled benzamide compounds of Formula (I) Formula (II) and Formula (III) and their radiolabeled nuclides and their pharmaceutically acceptable salts thereof as agents for diagnostic imaging and for detecting and treating cancer cells in living mammals.

The present invention also relates to a method of determining the proliferative effect and progression of a cancer in a living mammal.

A noninvasive novel method using novel benzamide compounds of Formula (I) Formula (II) and Formula (III) and their radiolabeled nuclides is provided to detect cancer cells and to assess the proliferative status of cancer cells which express sigma-2 ($\sigma_2$) receptors, such as cells of solid tumors, in vitro and in vivo.

In an aspect, Formula (I) Formula (II) and Formula (III) compounds are used to diagnose the presence of cancer in a living mammal or in a biological sample thereof. Formula (I) compounds include the compounds structurally shown of FIGS. 1, 2 and 3 and their pharmaceutically acceptable salts thereof, their radiolabeled counterparts and their mammalian metabolic derivatives. Formula (II) compounds and Formula (III) compounds include the compounds structurally shown of FIG. 7 and their pharmaceutically acceptable salts thereof, radiolabeled counterparts and their mammalian metabolic derivatives.

In an aspect, a method of detecting cancer comprises administering to a human patient afflicted with a solid tumor, such as breast cancer, a functionally effective amount of a detectably labeled conformationally-flexible benzamide compound having a structure of at least one of the structures illustrated in Formula (I) Formula (II) and Formula (III) and determining the extent to which the compound binds to cells of the cancer, the extent providing a measure of the presence and/or proliferative status of the cells, which status correlates to the extent of sigma-2 receptor expression by said cells. The method is based on the ability of the compounds illustratively depicted in FIGS. 1, 2, 3, and 7 to selectively bind to sigma-2 ($\sigma_2$) receptors versus $\sigma_1$ receptors.

In an aspect, a benzamide compound having a structure of one of the structures illustrated in Formula (I), Formula (II) and Formula (III) is radiolabeled as a radioligand. In an aspect the radioligand is an emitting radioligand.

Typically the label is a fluorescent label or radionuclide (M) such as a radioisotope of halogen ($^{125}I$, $^{123}I$, $^{124}I$, $^{76}Br$, $^{77}Br$, $^{18}F$) or ($^{11}C$). In an aspect a functional emitting effective amount of radiolabeled benzamide compound(s) is administered parenterally, i.e., by intravenous, i.p., intrathecal or enteral administration to a living mammal patient. In an aspect the radiolabeled emits a functional detectable amount of desired radioactivity. In a medical aspect the amount of emitted radioactivity is an amount which imparts a therapeutic benefit to the mammalian patient having cancer. In an aspect a therapeutic benefit is that benefit which is medicinally and therapeutically beneficial to the living mammalian afflicted with cancer. In an aspect a cytotoxic amount is an effective lethal amount of a therapeutic compound which beneficially kills or retards cancer cells.

In an aspect, unlabeled benzamide compounds having a structure of at least one of the structures depicted in Formula (I), Formula (II) and Formula (II) are used as precursor intermediates to make corresponding radiolabeled novel detectably labeled compounds or as sigma-2 specific ligands which can be used in competitive assays to assay for the presence of sigma-2 receptors as described hereinafter.

In an aspect a detectably labeled benzamide compound having a structure of at least one of the structures depicted in Formula (I), Formula (I) and Formula (III) is effectively administered to a living mammal or to a biological sample thereof or therefrom and the sample is analyzed and a diagnosis is made or obtained. In an aspect, a biological sample of the mammal comprises a representative sample taken of at least one of blood, vessels, atheroma, liver, and other body tissues a well as biopsies of body organs such as a liver biopsy or a muscle biopsy of a living mammal.

In an aspect the weight of a biological sample is a minimum of tissue about 1 mg, the amount of cells is about 2,000, and of blood about 2 µl or comparable functionally adequate amounts, quantities or volumes of other biological sample(s). In an aspect, the amount of biological sample is that amount or volume which is sufficient to provide for an analysis.

As used herein, the term "biological sample" or "biologic sample" includes a sample of a suitable size such as a sample of size and composition suitable to use in the methods disclosed herein.

Figure 6:
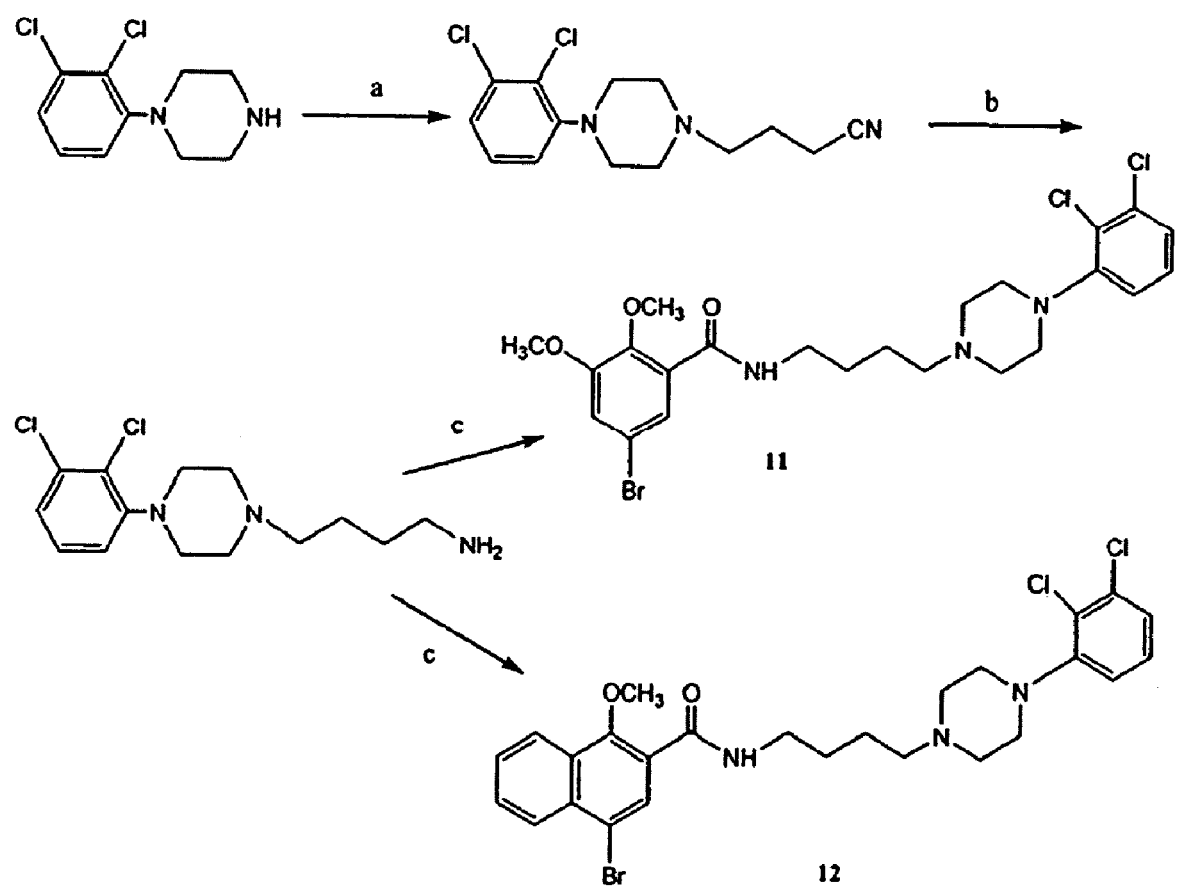
FIG. 6 shows an illustrative process for preparing novel conformationally flexible benzamide compounds (11 and 12) of Formula (I).

Novel processes for preparing novel benzamide compounds illustratively depicted having a structure of at least one of the structures depicted in Formula (I), Formula (II) and Formula (III) are provided in illustrative process preparation schematics in FIG. 4, FIG. 5 and FIG. 6 as further aspects of the invention and are illustrated by these procedures in which the meanings of the generic radicals are as noted above unless otherwise qualified.

For example, the reaction may conveniently be carried out under conditions similar to those described in Example 1.

Starting materials employed in the synthetic processes described above are commercially available, are reported in the scientific literature, or can be prepared using methods analogous to those described in the literature. The reaction conditions will be such as to allow a successful carrying out of the desired reaction to the desired degree of completion.

In instances where the novel benzamide compounds are sufficiently basic or acidic to form stable nontoxic acid or base salts, administration of the compounds as salts may be appropriate. Examples of pharmaceutically acceptable salts are organic acid addition salts formed with acids which produce a mammalian physiological acceptable anion, for example, tosylate, methanesulfonate, acetate, citrate, malonate, tartrate, succinate, benzoate, ascorbate, alpha-ketoglutarate, and alpha-glycerophosphate. Suitable inorganic salts include hydrochloride, sulfate, nitrate, bicarbonate, and carbonate salts.

In an aspect pharmaceutically acceptable salts are prepared using procedures well known in the art such as by reacting a basic compound such as an amine with a suitable acid to prepare a mammalian physiologically acceptable anion. Alkali metal (sodium, potassium or lithium) and alkaline earth metal (calcium, magnesium) salts can be made. In an aspect an oxalate salt is a pharmaceutically acceptable salt of a compound of Formula (I) Formula (II) and Formula (III). In an aspect an oxalate salt is prepared.

In an aspect, compounds having a structure illustrated in at least one of Formula (I), Formula (I) and Formula (III) are formulated as pharmaceutical compositions generally as their respective pharmaceutically acceptable salts and effectively administered to a mammalian host.

In an aspect a pharmaceutical composition is prepared comprising at least one compound having a structure depicted in at least one of the structures depicted in Formula (I), Formula (II) and Formula (III) as a radiolabeled benzamide compound.

In an aspect a living mammal host is selected from at least one of a human and non human animal such as canine, feline, equestrian, murine including dogs, cats, rabbits, guinea pigs, hamsters, mice, rats, horses, goats, sheep, pigs and cows. In an aspect a veterinarian treats a dog having cancer. In an aspect the mammal host is a patient.

In an aspect an inventive benzamide compound is systematically successfully administered, e.g., orally, in combination with a pharmaceutically acceptable vehicle such as an inert diluent or an assimilable mammalian edible carrier to the patient. The novel benzamide compound may be enclosed in a gelatin capsule, may be compressed into a tablet, or may be a part of the patient's diet. The compound may be combined with one or more compatible functional excipients and administered as ingestible tablets, buccal tablets, troches, capsules, elixirs, suspensions, syrups, wafers, crackers and pills. In an aspect the selected administration is, orally or parenterally, by intravenous, intramuscular, topical or subcutaneous routes of effective administration.

Pharmaceutical compositions may be used such as those formulated using readily available formulation ingredients with one or more benzamide radiolabeled compounds. In an aspect at least one novel benzamide compound having a structure depicted in FIGS. 1, 2, 3 and 7 is incorporated, optionally together with other active substances, with one or more conventional pharmacological acceptable carriers, diluents and/or excipients, to produce a conventional preparation(s) such as tablets, pills, powders, lozenges, sachets, cachets, elixirs, suspensions, emulsions, solutions, syrups, aerosols, ointments, gelatin capsules, suppositories, sterile injectable solutions and sterile packaged powders.

In an aspect, such compositions and preparations contain at least a pharmaceutically effective amount of the benzamide compound generally at least about 0.1% of the compound. The percentage of the compositions and preparations may, of course, be varied and may conveniently be dosage form about 2% to about 60% of the weight of a given unit dosage form. The amount of benzamide compound in such therapeutically useful compositions is such that an effective mammalian dosage level will be obtained for administration. In an aspect the amount is a threshold detectable amount. In an aspect the administration comprises two benzamide compounds. One or more of the benzamide compounds may be administered individually, serially, simultaneously, nearly simultaneous and sequentially. The compounds may be formulated as a time release composition if desired.

In an aspect, the preparations are consumed orally by a living mammal. In an aspect, the compositions are consumed orally by a human. In an aspect two compounds are administered to a living mammal.

In an aspect, depending on its form, the administered formulation may contain a binder, disintegrating agent, lubricant, sweetener, a liquid carrier. Pills may be coated or uncoated. A syrup may contain sucrose or fructose as a sweetener. Formulation ingredients used in preparing any unit dosage form should be pharmaceutically acceptable and substantially non-toxic in the amounts employed to a living mammal. In addition, if desired the compound may be incorporated into sustained-release preparations and administered using devices therefor. In an aspect an anti-microbial ingredient is included. In an aspect a preservative is included.

In an aspect, the benzamide compound is administered to a mammal as a pharmacologically acceptable composition such as in an aqueous composition. Pharmacologically acceptable compositions such as solutions of a benzamide compound or its salts can be prepared in water, optionally mixed with a nontoxic surfactant. Dispersions can also be prepared. Any pharmacologically suitable humane method of administration may be employed so that an effective radiolabeled amount of benzamide compound is made available to the biochemical system of the mammal.

In an aspect, the pharmaceutical dosage forms suitable for injection or infusion include sterile aqueous solutions or dispersions or sterile powders comprising a radiolabeled or unlabeled compound of Formula (I), Formula (II) and Formula (III) adapted for preparation of sterile injectable or infusible solutions or dispersions, optionally encapsulated in liposomes. The administered dosage form should be sterile, fluid and stable. The liquid carrier or vehicle can be a solvent or liquid dispersion medium comprising water, ethanol, a polyol, vegetable oils, and nontoxic glyceryl esters.

The fluidity of preparations can be maintained by the formation of liposomes and by the maintenance of the required particle size in the case of dispersions or by the use of surfactants. Antibacterial and antifungal agents may be employed. An isotonic agent such as an effective amount of a sugar, buffer or sodium chloride may be employed. Delaying absorption agents such as aluminum monostearate and gelatin may be employed if desired.

In an aspect sterile injectable solutions are prepared by incorporating the novel benzamide compound(s) in the desired amount in the appropriate solvent with other ingredients as required, followed by filter sterilization. In the case of sterile powders for the preparation of sterile injectable solutions, the preferred methods of preparation are vacuum drying and the freeze drying techniques, which yield a powder of the labeled or unlabeled compound of Formula (I), Formula (II) and Formula (III) along with any additional desired ingredient present in the previously sterile-filtered solutions.

For topical administration, a benzamide compound of Formula (I), Formula (II) and Formula (III) may be applied in pure form, i.e., when they are liquids. However, it will generally be desirable to administer them to the skin as compositions or formulations, in combination with a dermatologically acceptable carrier, which may be a solid or a liquid.

Useful effective dosages of the benzamide compounds of Formula (I), Formula (II) and Formula (III) can be determined by comparing their in vitro activity and in vivo activity using animal models. Methods for the extrapolation of effective dosages of some moieties in mice, and other animals, to humans are known for example, see U.S. Pat. No. 4,938,949.

In an aspect the amount of time elapsing between imagining is a time which provides for a useful and meaningful comparison of acquired images.

In an aspect the benzamide compound is applied as a radiolabeled benzamide compound.

Generally, the concentration of the benzamide compound(s) of Formula (I) Formula (II) and Formula (III) in a liquid composition, such as a lotion, will be from about 0.1-about 25 wt-%, preferably from about 0.5-about 10 wt-%. The concentration in a semi-solid or solid composition such as a gel or a powder will be about 0.1-about 5 wt-%, preferably about 0.5-about 2.5 wt-%. Single dosages for injection, infusion or ingestion will generally vary between 50-1500 mg, and may be administered, i.e., 1-3 times daily, to yield levels of about 0.5-50 mg/kg, for adult humans.

Accordingly, this discovery includes a pharmaceutical composition comprising a labeled or unlabeled compound of Formula (I) Formula (II) and Formula (III) as described hereinabove; or a pharmaceutically acceptable salt thereof, and as a pharmaceutically acceptable diluent or carrier.

In an aspect a pharmaceutically acceptable salt includes any water soluble salt which is pharmaceutically suitable to the mammalian recipient of the benzamide or radiolabeled compound. In an aspect a pharmaceutically acceptable diluent or carrier includes an aqueous diluent or any diluent or carrier which is innocuous to the mammal recipient of the benzamide compound and which provides for facilitation of the administration of the benzamide compound(s) and their radionuclide counterparts.

The precise dosage of the detectably labeled benzamide compound to be administered and the length of time over which administration is carried out will depend on a number of factors including the age and weight of the mammal patient and the route of administration.

In an aspect a therapeutic rate titration is performed wherein the living mammalian afflicted with cancer or believing to be so afflicted with cancer is administered a series of dosages and respective effects therefrom or thereafter are determined by an inventive method herein at respective dosages and times. In this manner a therapeutic dosage curve or titration is obtained for determining dosage for that mammal patient.

In an aspect, the radionuclide is purified.

Administration may be performed by local or systemic application as appropriate. Administration of compositions may be done by inhalation, orally, rectally or parenterally, such as by intramuscular, subcutaneous, intraarticular, intracranial, intradermal, intraocular, intraperitoneal, intrathecal and intravenous injection. The injection may be by stereotaxic injection. Local administration may also be performed, e.g. at an affected site e.g. by use of a catheter or syringe. Treatment by topical application of a composition, e.g. an ointment, to the skin is appropriate. Administration may be performed at intervals of time, such as two or more applications, at some intervals, such as several times a day, or at periodic intervals of the daily or daily.

Compounds of Formula (I) Formula (II) and Formula (III) can be suitably radiolabeled using any of a number of techniques which are well known in the art. For example, a radioisotope can be incorporated into said compound or appended to said compound of Formula (I) using techniques well known in the art, for example, techniques analogous to those described in Arthur Murry III, D. Lloyd Williams; Organic Synthesis with Isotopes, vol. I and II, Interscience Publishers Inc., N.Y. (1958) and Melvin Calvin et al. Isotopic Carbon John Wiley and Sons Inc., N.Y. (1949). Preferably, a compound of Formula (I) may be labeled effectively by appending a radioisotope of a halogen to the aromatic rings comprising Ar, Ar' and Ar". In an aspect compounds of Formula (I), Formula (II) and Formula (III) are radiolabeled prior to formulation and administration.

Additionally, a benzamide compound of Formula (I), Formula (II) and Formula (III) can be labeled with a metal chelating group optionally comprising a radionuclide, such as a metallic radioisotope. Such chelating groups are well known in the art and include polycarboxylic acids such as for example diethylenetriaminepentaacetic acid, ethylenediaminetetraacetic acid, and the like, or analogs or homologs thereof, as well as the chelating groups disclosed in Anderson and Welch (Chem. Rev. 99: 2219-2234, 1999) and Jurisson and Lydon (Chem. Rev. 99: 2205-2218, 1999).

The chelating group or the radionuclide therein may be attached directly to a compound of Formula (I), Formula (II) and Formula (III) or may be attached to a compound of Formula (I), Formula (II) and Formula (III) by means of a divalent or bifunctional organic linker group. Such bifunctional organic linker groups are well known in the art and are preferably less than about 50 angstroms in length. Examples of suitable bifunctional linker groups include 2-carboxymethyl, 3-carboxypropyl, 4-carboxybutyl, and the like. Preferably, the bifunctional linker group is attached to a compound of Formula (I) at the amino nitrogen which is substituted by the group, NRR' in Formula (I). The linker group may also be attached at any synthetically feasible position. For example, FIG. 7 shows two compounds of the invention (compounds II and III) which are compounds of Formula (I), labeled with a metal chelating group comprising a radionuclide (M).

Any metallic radioisotope capable of being detected in a PET or SPECT or MicroPET® diagnostic imagining procedure can be employed as a functional radionuclide.

Suitable nonlimiting examples of useful radionuclides include: $^{225}$Ac, $^{211}$At, $^{212}$Bi, $^{213}$Bi, $^{75}$Br, $^{76}$Br, $^{11}$C, $^{141}$Ce, $^{51}$Cr, $^{60}$Cu, $^{61}$Cu, $^{62}$Cu, $^{64}$Cu, $^{67}$Cu, $^{166}$Dy, $^{18}$F, $^{152}$Gd, $^{153}$Gd, $^{195m}$Au, $^{166}$Ho, $^{111}$In, $^{113m}$In, $^{123}$I, $^{124}$I, $^{121}$I, $^{55}$Fe, $^{59}$Fe, $^{177}$Lu, $^{13}$N, $^{15}$O, $^{103}$Pd, $^{223}$Ra, $^{224}$Ra, $^{186}$Re, $^{188}$Re, $^{81}$Rb, $^{82}$Rb, $^{86}$Rb, $^{103}$Ru, $^{106}$Ru, $^{153}$Sm, $^{46}$Sc, $^{178}$Ta, $^{94m}$Tc, $^{99m}$Tc, $^{201}$Tl, $^{45}$Ti, $^{169}$Yb, $^{86}$Y, $^{90}$Y, and $^{89}$Zr. In an aspect technetium-99m is used for SPECT imaging studies, and rhenium-188, rhenium-186, copper-64 and yitrium-90 are useful for radiotherapy of breast tumors. In an aspect the compounds of Formula (I), Formula (II) and Formula (III) including compound 23 are radiolabeled with at least one of tritium and iodine 125 radiolabels using standard radiolabeling conditions to produce at least one of a tritiated and iodine 125 labeled analog that can be used in the in vitro detection of sigma 2 receptors in tumors and normal tissue.

PET (or "Positron Emission Tomography"), and SPECT are non-invasive molecular diagnostic imaging (standard) medical procedures that produce (i.e. capture and optionally record) multiple acquisitions i.e. images of the body's biological functions and in an aspect are used to determine the extent of malignant disease. In an aspect, these imaging procedures show the presence and distribution of a radiolabeled detectable functionally emitting radiolabeled chemical i.e. a radionuclide acquisitioned at various selected times. Advantageously these two imaging procedures depict both metabolic characteristics of tissues and changes therein.

In an aspect, positive emission tomography (PET imaging) comprises detection of γ-rays emitted from radionuclides such as $^{76}$Br Compound 6, $^{123}$I Compound 6, $^{124}$I Compound 6, $^{125}$I Compound 6 and $^{11}$C Compound 10, that decay by positron emission and are located within a mammalian patient's body. In an aspect this is possible by virtue of administration of a radiolabeled benzamide compound to the patient.

In an aspect, single photon emission computed tomography ("SPECT imaging") comprises a collimation of gamma rays emitted by a radiopharmaceutical distribution such as detectable radioactivity emitting a benzamide compound of the invention or a pharmaceutical composition comprising a novel benzamide compound within the mammalian body undergoing treatment and analysis. Generally collimators for SPECT imaging are lead and comprise thousands of various shaped parallel channels through which—and only through which—gamma rays are allowed to pass. Generally such collimators are positioned over a single crystal of NaI contained in the Gamma camera in an arrangement referred to as an Anger camera, (http://www.amershamhealth.com/medcyclopaedia/Volume %20I/Anger %20camera). The image or acquisition from the camera is the captured image which is presented to a human operator as part of a viewable image. This may be a screen shot or a captured digital image, which may be stored in a computer storage. In an aspect multi-acquisition is used. In an aspect a multi-acquisition is carried out over an elapsed time interval.

Single-photon emission computerized tomography (SPECT) scan creates three-dimensional images of internal organs revealing anatomy and function. A tiny amount of radioactive tracer is injected through a vein and a camera detects the radiation emitted by these tracers.

In an aspect an external measurement is made of the two high energy photons emitted in opposite directions when a positron-emitting radionuclide decays in a patient. A large number of scintillation detectors detect these photon pairs and measure the sum of radioactivity along many different paths through the patient undergoing measurement. Appropriate software associated with the operating instrument reconstructs a three-dimensional image of the patient and the concentrations of radionuclides can be expressed in quantitative units of radiotracer concentration per ml of tissue.

In an aspect images are acquisitioned (taken) over elapsed time in dynamic fashion to assemble a developing or developed scenario of developing or changing situations in the mammalian patient. It is believed that the tumorous or cancerous areas have a higher density of these receptors than surrounding normal tissue and thus that is why such areas show up on the image.

In an aspect a PET and/or a SPECT image is taken of a living mammal after administration of a compound of Formula (I) Formula (II) and Formula (III) to a living mammal. The image may be retained in computer storage if desired. A number of images may be acquired as a function of elapsed time to produce a profile over time of the images.

In an aspect a radioactive substance is produced in a process and is attached, or tagged, to a benzamide compound referred to as radiolabeling. After this radiolabeled benzamide as compound 6 labeled with one of $^{76}$Br, $^{123}$I, $^{124}$I, $^{125}$I or compound 10 labeled with $^{11}$C is administered to a patient, radioactivity travels through gastrointestinal tract through the vascular circulator (blood) system of the body and localizes in the appropriate areas of the body and is detected by PET or SPECT scanner.

Typically an adequate amount of time is allowed to lapse for the treated living mammal (i.e. having received the radiolabeled benzamide) to come to an equilibrium state following satisfactory administration of the benzamide radioligand to the mammal. Typically the mammal is placed in a position near the PET instrument or SPECT instrument or Micro-PET® instrument allowing satisfactory operation of the PET instrument and/or SPECT instrument. The PET and SPECT instruments are equipped with all necessary operable software and operation requirements. These instruments are turned on by supplying 100 volts electric power to the instruments.

Generally after mammal has received its administration of the radiolabeled benzamide the mammal is placed in/on the PET scanner, which has a opening in the middle. In the PET scanner there are multiple rings of detectors that record the emission of energy from the radioactive substance now within in the mammal. In an aspect the mammal is comfortably moved into the hole of the machine. The images are displayed on the monitor of a computer, suitably equipped and operably coupled to the PET scanner instrument for acquiring.

Examples 1-5 following are illustrative of but are not meant to be limiting of this discovery.

EXAMPLES

Example 1

Synthesis of target tetrahydroisoquinoline analogs is shown in FIG. 4 and FIG. 5. Reaction of the secondary amine of compounds 13 and 14 with either bromoacetonitrile or bromobutyronitrile gave N-alkylated products, 15, 16, 17, and 18, in 75-85% yield. Reduction with either lithium aluminum hydride in THF or hydrogenation over palladium on charcoal gave the corresponding amines, 19, 20, 21, 22, in quantitative yields. Condensation of amines 19, 20, 21, 22 with either 2-methoxy-5-bromonaphthoyl chloride or 5-bromo-2,3-dimethoxybenzoic acid gave the corresponding amide analogs, 1, 2, 3, 4, 5, 6, in excess of 90% yield. Condensation of amines 19, 21 and 22 with either 5-bromo-2-methoxybenzoic acid or 5-methyl-2-methoxybenzoic acid gave amides 7, 8, 9, and 10 in excess of 90% yield. Synthesis of the 2,3-dichlorophenylpiperazine benzamide and naphthamide analogs, 11 and 12, was accomplished using a similar reaction sequence as outlined in FIG. 5.

Example 2

Physical Data

The following physical data was obtained for and identifies and characterizes benzamide compounds and attests to their preparation denoted respectively by numbers (1, 2, 3, 4, 5, 6, 7, 8, 9, 10, 11 and 12) herein. For example the immediately following paragraph presents the melting point of the respective oxalate salt, the results of a NMR (nuclear magnetic resonance analysis) and comparison calculated and observed molecular weights.

Physical Data for Compound 1. MP (Melting Point) 142° C.-144° C. (oxalate salt); $^1$H-NMR (d$_6$-DMSO) δ 2.99 (s, 2H), 3.10 (s, 2H), 3.61-3.63 (m, 3H), 3.73 (s, 3H), 3.85 (s, 3H), 4.15 (s, 3H), 7.13-7.23 (m, 4H), 7.34 (s, 1H), 7.36 (s, 1H), 8.59 (t, J=5.0 Hz, 1H). Calculated: C, 51.88; H, 4.95; N, 5.50. Observed: C, 51.73; H, 4.95; N, 5.51.

Physical Data for Compound 2. MP 91° C.-93° C. (oxalate salt); $^1$H-NMR (d$_6$-DMSO) δ 2.92 (s, 2H), 3.13 (s, 2H), 3.59-3.63 (m, 3H), 3.71 (s, 3H), 3.73 (s, 3H), 3.74 (s, 3H), 3.85 (s, 3H), 4.10 (s, 3H), 6.72 (s, 1H), 6.78 (s, 1H), 7.34 (s, 1H), 7.37 (s, 1H), 8.60 (s, 1H). Calculated: C, 50.63; H, 5.13; N, 4.92. Observed: C, 50.49; H, 5.30; N, 4.60.

Physical Data for Compound 3. MP 180° C.-182° C. (oxalate salt); $^1$H-NMR (d$_6$-DMSO) δ 3.02 (s, 2H), 3.19 9s, 2H), 3.72-3.74 (m, 3H), 3.94 (s, 3H), 4.21 (s, 3H), 7.16-7.25 (m, 4H), 7.75 (t, J=8.1 Hz, 1H), 7.81 (t, J=8.1 Hz, 1H), 8.05 (s, 1H), 8.15 (d, J=8.3 Hz, 1H), 8.24 (d, J=8.3 Hz, 1H), 8.77 (t, J=5.4 Hz, 1H). Calculated: C, 56.72; H, 4.76; N, 5.29. Observed: C, 56.50; H, 4.91; N, 5.14.

Physical Data for Compound 4. MP 187° C.-189° C. (oxalate salt); $^1$H-NMR (d6-DMSO) δ 2.94 (s, 3H), 3.19 (s, 4H), 3.71 (s, 3H), 3.73 (s, 3H), 3.94 (s, 3H), 4.12 (s, 3H), 6.74 (s, 1H), 6.79 (s, 1H), 7.75 (t, J=7.6 Hz, 1H), 7.82 (t, J=7.6 Hz, 1H), 8.05 (s, 1H), 8.15 (d, J=8.3 Hz, 1H), 8.25 (d, J=8.3 Hz, 1H), 8.76 (s, 1H). Calculated: C, 55.02; H, 4.96; N, 4.75. Observed: C, 54.76; H, 5.04; N, 4.65.

Physical Data for Compound 5. MP 165° C.-167° C. (oxalate salt); $^1$H-NMR (d6-DMSO) δ 1.61-1.80 (m, 4H), 2.96 (s, 2H), 3.36-3.39 (m, 5H), 3.71 (s, 3H), 3.73 (s, 3H), 3.95 (s, 3H), 4.19 (s, 3H), 6.77 (s, 1H), 6.80 (s, 1H) 7.75 (t, J=7.4 Hz, 1H), 7.81 (t, J=7.4 Hz, 1H), 7.95 (s, 1H), 8.15 (d, J=8.3 Hz, 1H), 8.25 (d, J=8.3 Hz, 1H), 8.60 (t, J=5.6 Hz, 1H). Calculated: C, 56.41; H, 5.39; N, 4.54. Observed: C, 56.32; H, 5.45; N, 4.45.

Physical Data for Compound 6. $^1$H-NMR (CDCl$_3$) δ 1.70-1.79 (m, 4H), 2.59 (s, 2H), 2.73-2.76 (m, 2H), 2.81-2.84 (m, 2H), 3.51-3.52 (m, 2H), 3.58 (s, 2H), 3.85 (s, 3H), 3.86 (s, 3H), 3.88 (s, 3H), 3.90 (s, 3H), 6.52 (s, 1H), 6.60 (s, 1H), 7.12 (d, J=2.7 Hz, 1H), 7.78 (d, J=2.7 Hz, 1H), 8.05 (s, 1H).

Physical Data for Compound 7. MP 166° C.-168° C. (oxalate salt); $^1$H-NMR (d6-DMSO) δ 3.02 (s, 3H), 3.14 (s, 2H), 3.66 (s, 2H), 3.83 (s, 3H), 4.19 (s, 3H), 7.12-7.25 (m, 5H), 7.65-7.67 (m, 1H), 7.86 (s, 1H), 8.56 (t, J=5.4 Hz, 1H).

Calculated: C, 52.62; H, 4.84; N, 5.84. Observed: C, 52.38; H, 4.75; N, 5.69.

Physical Data for Compound 8. MP 158° C.-160° C. (oxalate salt); $^1$H-NMR (d6-DMSO) δ 2.93 (s, 2H), 3.16 (s, 2H), 3.60-3.66 (m, 3H), 3.71 (s, 3H), 3.73 (s, 3H), 3.84 (s, 3H), 4.14 (s, 3H), 6.73 (s, 1H), 6.78 (s, 1H), 7.13 (d, J=8.9 Hz, 1H), 7.66 (d, J=8.7 Hz, 1H), 7.86 (s, 1H), 8.57 (t, J=5.4 Hz, 1H). Calculated: C, 51.22; H, 5.05; N, 5.19. Observed: C, 51.23; H, 5.07; N, 5.04.

Physical Data for Compound 9. MP 160° C.-162° C. (oxalate salt); $^1$H-NMR (d6-DMSO) d 2.27 (s, 3H), 2.94 (s, 2H), 3.16 (s, 2H), 3.65-3.66 (m, 3H), 3.72 (s, 3H), 3.73 (s, 3H), 3.82 (s, 3H), 4.14 (s, 3H), 6.73 (s, 1H), 6.79 (s, 1H), 7.03 (d, J=8.4 Hz, 1H), 7.29 (d, J=8.4 Hz, 1H), 7.63 (s, 1H), 8.51 (s, 1H). Calculated: C, 60.18; H, 6.42; N, 5.85. Observed: C, 60.32; H, 6.39; N, 5.56.

Physical Data for Compound 10. $^1$H-NMR (CDCl$_3$) δ 1.70-1.79 (m, 4H), 2.32 (s, 3H), 2.59 (s, 2H), 2.73-2.76 (m, 2H), 2.81-2.84 (m, 2H), 3.51-3.52 (m, 2H), 3.58 (s, 2H), 3.81 (s, 3H), 3.83 (s, 3H), 3.89 (s, 3H), 6.50 (s, 1H), 6.58 (s, 1H), 6.86-6.96 (m, 2H), 7.11 (s, 1H), 8.00 (s, 1H).

Physical Data for Compound 11. $^1$H-NMR (CDCl$_3$) δ 1.66 (s, 4H), 2.44-2.66 (m, 6H), 3.06 (s, 2H), 3.17-3.21 (m, 2H), 3.48-3.50 (m, 2H), 3.88 (s, 6H), 6.76-6.96 (m, 2H), 7.12-7.16 (m, 2H), 7.77-7.79 (m, 1H), 7.99 (s, 1H).

Physical Data for Compound 12. $^1$H-NMR (CDCl$_3$) δ 1.72 (s, 4H), 2.47-2.67 (m, 6H), 3.03 (s, 2H), 3.15-3.20 (m, 2H), 3.54-3.63 (m, 2H), 3.99 (s, 3H), 6.73-6.93 (m, 2H), 7.11-7.17 (m, 1H), 7.60-7.72 (m, 2H), 8.01-8.26 (m, 3H), 8.38 (s, 1H).

Physical data for Compound 23. $^1$H-NMR (CDCl$_3$) δ 1.60-1.70 (m, 4H), 2.33 (s, 3H), 2.51-2.56 (t, 2H), 2.67-2.72 (t, 2H), 2.78-2.83 (t, 2H), 3.48-3.54 (m, 4H), 3.82-3.83 (s, 6H), 4.21-4.25 (t, 1H), 4.30-4.34 (t, 1H), 4.68-4.72 (t, 1H), 4.84-4.88 (t, 1H), 6.49 (s, 1H), 6.57 (s, 1H), 6.99-6.83 (d, 1H), 7.19-7.30 (d, 1H), 7.95 (s, 1H), 7.99 (d, 1H).

Example 3 σ Receptor Binding Assays

The σ$_1$ receptor binding assay was conducted using guinea pig brain membrane homogenates (100 μg protein). Membrane homogenates were incubated with 3 nM [$^3$H](+)-pentazocine (31.6 Ci/mmol) in 50 mM Tris-HCl (pH 8.0) at 25° C. for either 120 or 240 min. Test compounds were dissolved in ethanol then diluted in buffer for a total incubation volume of 0.5 ml. Test compounds were added in concentrations ranging from 0.005 to 1000 nM. Assays were terminated by the addition of ice-cold 10 mM Tris-HCl (pH 8.0) followed by rapid filtration through Whatman GF/B glass fiber filters (presoaked in 0.5% polyethylenimine) using a Brandel cell harvester (Gaithersburg, Md.). Filters were washed twice with 5 ml of ice cold buffer. Nonspecific binding was determined in the presence of 10 μM (+)-pentazocine. Liquid scintillation counting was carried out in EcoLite(+) (ICN Radiochemicals; Costa Mesa, Calif. now Valeant Pharmaceuticals International, Valeant Plaza, 3300 Hyland Avenue, Costa Mesa, Calif. 92626 USA), using a Beckman LS 6000IC spectrometer with a counting efficiency of 50%.

The σ$_2$ receptor binding assay was conducted using rat liver membrane homogenates (35 μg of protein). Membrane homogenates were incubated with 3 nM [$^3$H]DTG (38.3 Ci/mmol) in the presence of 100 nM (+)-pentazocine to block σ$_1$ sites. Incubations were carried out in 50 mM Tris-HCl (pH 8.0) for 120 min at 25° C. in a total incubation volume of 0.5 ml. Test compounds were added in concentrations ranging from 0.005 to 1000 nM. Assays were terminated by the addition of ice-cold 10 mM Tris-HCl (pH 8.0) followed by rapid filtration through Whatman GF/B glass fiber filters (presoaked in 0.5% polyethylenimine) using a Brandel cell harvester (Brandel, 8561 Atlas Dr., Gaithersburg, Md. 20877, USA). Filters were washed twice with 5 ml of ice cold buffer. Nonspecific binding was determined in the presence of 5 μM DTG. Liquid scintillation counting was carried out in EcoLite (+) (ICN Radiochemicals; Costa Mesa, Calif., now Valeant Pharmaceuticals International, Valeant Plaza, 3300 Hyland Avenue, Costa Mesa, Calif. 92626 USA) using a Beckman LS 6000IC spectrometer with a counting efficiency of 50%.

The IC$_{50}$ values at sigma sites were generally determined in triplicate from non-linear regression of binding data as analyzed by JMP (SAS InstituteIncv., JMP Software, SAS Campus Drive; Cary, N.C. 27513), using 8 concentrations of each compound. K$_i$ values were calculated using the method of Cheng-Prusoff (Biochem. Pharmacol. 1973, 22, 3099-4022) and represent mean values.±SEM. All curves were best fit to a one site fit and gave Hill coefficients of 0.8-1.0. The K$_d$ value used for [$^3$H]DTG in rat liver was 17.9 nM and was 4.8 nM for [$^3$H](+)-pentazocine in guinea pig brain.[11,12]

Generally compounds of the invention demonstrate high selectivity for sigma-2 versus sigma-1 receptors (Table).

Example 4

The σ$_2$ radioligand ([$^{76}$Br]6), was labeled with $^{76}$Br via an electrophilic destannylation reaction. The reaction takes place under aqueous (200 μL Milli-Q) conditions in the presence of 5% peracetic acid/acetic acid (40 μL) for 40 min. (A) was purified via HPLC with yields typically between 50-60%.

This compound was studied in mature Balb/C mice that were implanted with EMT-6 mammary tumors. The mice were implanted in the nape of the neck 7 days prior to the study. The biodistribution study consisted of three groups: 1 hr low dose (≈6 μCi), 4 hr low dose and a 4 hr high dose (≈150 μCi). The % ID/g at 1 hr for tumor, brain, fat, blood and liver were 4.0±0.4, 0.25±0.02, 1.1±0.4, 2.1±0.3 and 5.4±0.4, respectively. At 4 hr for the low dose animals the values decreased to 1.2±0.2, 0.15±0.02, 0.3±0.2, 0.82±0.08 and 1.3±0.2, respectively. The % ID/g for the 4 hr high dose animals was not significantly different. The activity injected into the high dose animals was enough to perform Micro-PET® imaging studies. At 1 and 2 hr the tumors were clearly identified in the three animals that were injected. This initial study has shown that this σ$_2$ receptor compound has a high uptake into EMT-6 mammary tumors and can be imaged non-invasively. (MicroPET® is a dedicated PET scanner designed for high resolution imaging of small laboratory animals. It is available from Concorde Microsystems, Inc. 10427 Cogdill Rd, Suite 500 Knoxville, Tenn. 37932 USA.)

Without being bound by theory, it is believed that compounds of Formula (I), Formula (II) and Formula (III) when labeled with detectable radionuclides provide detectably labeled ligands that selectively bind to cancer cells and can be quantified by using one or more of functional imaging techniques such as positron emission tomography (PET), including MicroPET®, single photon emission computed tomography (SPECT), MRI, computed tomography (CT) and functional magnetic resonance imaging (fMRI). Said components have the potential to noninvasively assess the proliferative status of known or suspected tumor cells or cells subject to hyperplasia, in bladder, colon, prostate, breast, lung, gut, pancreas, reproductive system, brain and the like. The labeled compounds having a structure illustrated in Formula (I) can also be used to treat cancer or abnormally dividing cells, by selectively inhibiting their proliferation.

The benzamides of Formula (I) are useful as radiotracers for imaging dopamine D3 receptors with PET including compound 11 (Table IA and Table 2).

Since many of the compounds (1-12) depicted in Table IA have a high affinity for dopamine D3 receptors, they are useful in the treatment of affective disorders such as schizophrenia, and depression as well as movement disorders such as Parkinson's Disease.

Example 5

Biological Data

This section focuses on the use of the sigma-2 ($\sigma_2$) receptor as a biomarker of tumor proliferation. This is based on inventor data demonstrating that $\sigma_2$ receptors are expressed in about 10-fold higher density in proliferative mouse mammary adenocarcinoma cells versus the nonproliferative or quiescent cell population under both in vitro (cell culture) and in vivo (tumor xenografts) conditions. Therefore, a $\sigma_2$ receptor PET radiotracer has the potential to provide information regarding the proliferative status of breast cancer. An in vivo imaging procedure that can provide information about the proliferative status of primary breast tumors would represent a significant improvement over current methods used in making this assessment. Our preliminary data also indicate that $\sigma_2$-selective radiotracers are predicted to have a better tumor:non-tumor ratio than other agents, such as FDG and the DNA precursors, currently used to assess proliferation in PET oncology studies.

A. Carbon-11 labeled analogs. The inventors identified a number of lead compounds having a high affinity and selectivity for $\sigma_2$ versus $\sigma_1$ receptors (Table I). The presence of a 2-methoxy group in the lead compounds indicates that it is possible to prepare a $^{11}$C-labeled version of the $\sigma_2$ ligands using standard radiochemistry procedures. This was accomplished via O-alkylation of the phenol precursor. The overall yield (15-75% from [$^{11}$C]methyl iodide) and specific activity (1000-4000 mCi/μmol) of each radiotracer was suitable for in vivo studies.

TABLE I

| # | X | R | n | $\sigma_1$ | $\sigma_2$ | $\sigma_1$:$\sigma_2$ Ratio | % Yield | Specific Activity (EOB) |
|---|---|---|---|---|---|---|---|---|
| 9 | H | CH$_3$ | 2 | 10,412 | 13.3 | 783 | 60-75 | ≈5,000 mCi/μmol |
| 10 | H | CH$_3$ | 4 | 3,078 | 10.3 | 300 | 60-75 | ≈4,000 mCi/μmol |
| 8 | H | Br | 2 | 5,484 | 12.2 | 442 | 10-15 | ≈1,000 mCi/μmol |
| 6 | OCH$_3$ | Br | 4 | 12,900 | 8.2 | 1,573 | 30-40 | ≈4,000 mCi/μmol |

B. Biodistribution Studies of $^{11}$C analogs in Tumor-Bearing Mice. Biodistribution studies were conducted in mature Balb/c mice that were implanted with EMT-6 mammary tumors identified herein as EMT-6 BALB/C mice to create laboratory tumor-bearing mice. The mice were implanted in the scapular region seven days prior to the study. Animals were injected with 100-150 μCi of the $^{11}$C-labeled radiotracer and the animals were sacrificed at 5, 30, and 60 min post-i.v. injection of the radiotracer.

The results of the biodistribution studies are given respectively in Tables II-V following.

TABLE II

[$^{11}$C]9 Biodistribution in EMT-6 BALB/C mice

| | 5 min | 30 min | 1 hour |
|---|---|---|---|
| % ID per gram | | | |
| blood | 5.89 ± 0.29 | 2.62 ± 0.22 | 1.98 ± 0.35 |
| lung | 5.69 ± 0.70 | 1.42 ± 0.15 | 1.39 ± 0.67 |
| liver | 18.49 ± 2.87 | 3.87 ± 0.67 | 1.70 ± 0.23 |
| kidney | 44.07 ± 1.67 | 2.77 ± 0.42 | 1.01 ± 0.12 |
| muscle | 1.75 ± 0.21 | 0.56 ± 0.19 | 0.41 ± 0.22 |
| fat | 3.07 ± 0.40 | 0.38 ± 0.12 | 0.26 ± 0.09 |
| heart | 2.89 ± 0.36 | 0.76 ± 0.06 | 0.76 ± 0.46 |
| brain | 1.63 ± 0.30 | 0.11 ± 0.01 | 0.10 ± 0.04 |
| tumor | 3.10 ± 0.25 | 1.08 ± 0.08 | 0.85 ± 0.14 |
| ratio | | | |
| Tumor:blood | 0.53 ± 0.04 | 0.41 ± 0.02 | 0.44 ± 0.06 |
| Tumor:lung | 0.55 ± 0.07 | 0.77 ± 0.14 | 0.68 ± 0.19 |
| Tumor:muscle | 1.79 ± 0.20 | 2.08 ± 0.59 | 2.40 ± 0.84 |
| Tumor:fat | 1.03 ± 0.21 | 3.10 ± 1.21 | 3.46 ± 0.91 |
| Tumor:heart | 1.08 ± 0.10 | 1.43 ± 0.14 | 1.32 ± 0.45 |

TABLE III

[$^{11}$C]10 Biodistribution in EMT-6 BALB/C mice

| | 5 min | 30 min | 1 hour |
|---|---|---|---|
| % ID per gram | | | |
| blood | 3.09 ± 0.33 | 1.31 ± 0.11 | 0.73 ± 0.05 |
| lung | 14.02 ± 1.40 | 2.27 ± 0.42 | 1.09 ± 0.26 |
| liver | 12.32 ± 1.73 | 9.65 ± 2.00 | 3.00 ± 0.21 |
| kidney | 20.50 ± 1.86 | 4.12 ± 0.51 | 2.26 ± 0.36 |
| muscle | 4.49 ± 0.45 | 0.75 ± 0.13 | 0.49 ± 0.11 |
| fat | 1.88 ± 0.50 | 0.68 ± 0.19 | 0.33 ± 0.24 |
| heart | 5.86 ± 0.47 | 0.95 ± 0.17 | 0.50 ± 0.11 |
| brain | 2.29 ± 0.28 | 0.28 ± 0.03 | 0.15 ± 0.01 |
| tumor | 4.22 ± 1.01 | 2.35 ± 0.27 | 1.32 ± 0.17 |
| ratio | | | |
| Tumor:blood | 1.37 ± 0.33 | 1.80 ± 0.26 | 1.81 ± 0.11 |
| Tumor:lung | 0.31 ± 0.11 | 1.06 ± 0.24 | 1.28 ± 0.41 |
| Tumor:muscle | 0.93 ± 0.13 | 3.18 ± 0.51 | 2.78 ± 0.62 |
| Tumor:fat | 2.28 ± 0.32 | 3.68 ± 1.14 | 5.36 ± 2.38 |
| Tumor:heart | 0.71 ± 0.12 | 2.53 ± 0.55 | 2.78 ± 0.79 |

TABLE IV

[$^{11}$C]8 Biodistribution in EMT-6 BALB/C mice

| | 5 min | 30 min | 1 hour |
|---|---|---|---|
| % ID per gram | | | |
| blood | 5.25 ± 0.39 | 2.35 ± 0.16 | 1.88 ± 0.16 |
| lung | 5.72 ± 0.40 | 1.83 ± 0.13 | 1.32 ± 0.11 |
| liver | 19.88 ± 3.10 | 5.89 ± 0.82 | 2.65 ± 0.29 |

TABLE IV-continued

[11C]8 Biodistribution in EMT-6 BALB/C mice

| | 5 min | 30 min | 1 hour |
|---|---|---|---|
| kidney | 51.03 ± 7.14 | 34.19 ± 1.74 | 19.78 ± 1.99 |
| muscle | 1.73 ± 0.11 | 0.52 ± 0.23 | 0.36 ± 0.08 |
| fat | 2.05 ± 0.49 | 0.63 ± 0.19 | 0.37 ± 0.13 |
| heart | 3.18 ± 0.26 | 0.77 ± 0.08 | 0.56 ± 0.05 |
| brain | 2.52 ± 0.15 | 0.26 ± 0.10 | 0.14 ± 0.02 |
| tumor | 1.82 ± 0.39 | 1.06 ± 0.09 | 0.87 ± 0.09 |
| ratio | | | |
| Tumor:blood | 0.35 ± 0.07 | 0.45 ± 0.05 | 0.46 ± 0.02 |
| Tumor:lung | 0.32 ± 0.06 | 0.58 ± 0.07 | 0.66 ± 0.03 |
| Tumor:muscle | 1.05 ± 0.21 | 2.24 ± 0.63 | 2.52 ± 0.66 |
| Tumor:fat | 0.93 ± 0.27 | 1.76 ± 0.40 | 2.64 ± 1.12 |
| Tumor:heart | 0.57 ± 0.09 | 1.39 ± 0.17 | 1.56 ± 0.16 |

TABLE V

[11C]6 Biodistribution in EMT-6 BALB/C mice

| | 5 min | 30 min | 1 hour |
|---|---|---|---|
| % ID per gram | | | |
| blood | 7.12 ± 1.01 | 0.99 ± 0.15 | 0.45 ± 0.04 |
| lung | 6.01 ± 0.77 | 1.34 ± 0.23 | 0.70 ± 0.26 |
| liver(all) | 25.02 ± 3.70 | 2.48 ± 0.52 | 1.19 ± 0.17 |
| kidney | 19.48 ± 1.46 | 2.57 ± 0.78 | 1.34 ± 0.19 |
| muscle | 1.94 ± 0.13 | 1.67 ± 0.14 | 0.26 ± 0.07 |
| fat | 1.66 ± 0.41 | 0.46 ± 0.19 | 0.20 ± 0.08 |
| heart | 3.54 ± 0.31 | 0.68 ± 0.12 | 0.29 ± 0.10 |
| brain | 0.33 ± 0.09 | 0.10 ± 0.00 | 0.03 ± 0.00 |
| tumor | 2.82 ± 0.36 | 0.92 ± 0.10 | 0.50 ± 0.09 |
| ratio | | | |
| Tumor:blood | 0.40 ± 0.01 | 0.94 ± 0.05 | 1.10 ± 0.11 |
| Tumor:lung | 0.47 ± 0.04 | 0.69 ± 0.08 | 0.79 ± 0.30 |
| Tumor:muscle | 1.46 ± 0.19 | 0.59 ± 0.05 | 1.84 ± 0.25 |
| Tumor:fat | 1.82 ± 0.45 | 2.05 ± 0.57 | 2.77 ± 0.82 |
| Tumor:heart | 0.80 ± 0.07 | 1.36 ± 0.12 | 1.86 ± 0.64 |

C. Synthesis of Radiohalogenated $\sigma_2$ Receptor Ligands and in vivo studies. The presence of a bromine atom in compounds 8 and 6 (Table I) indicates that it is possible to prepare radiohalogenated probes of the $\sigma_2$ receptors by isotopic substitution with B-76, or by replacing the bromine atom with I-125. This was accomplished by preparing the corresponding tin precursor and conducting the oxidative radiohalogenation reactions outlined in Schemes I and II. The $^{125}$I-labeled analogs, 6i and 8i, were obtained in an overall yield of 50% and a specific activity of 2200 mCi/μmol. Similarly, the $^{76}$Br-labeled analogs of 5 and 7 were obtained in a yield of 50-60% and a specific activity >1,000 mCi/μmol.

Scheme I

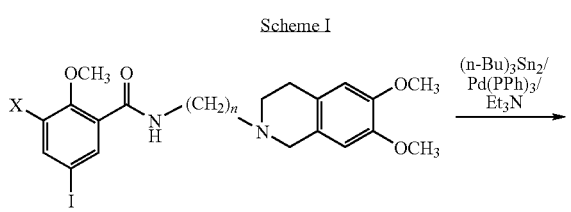

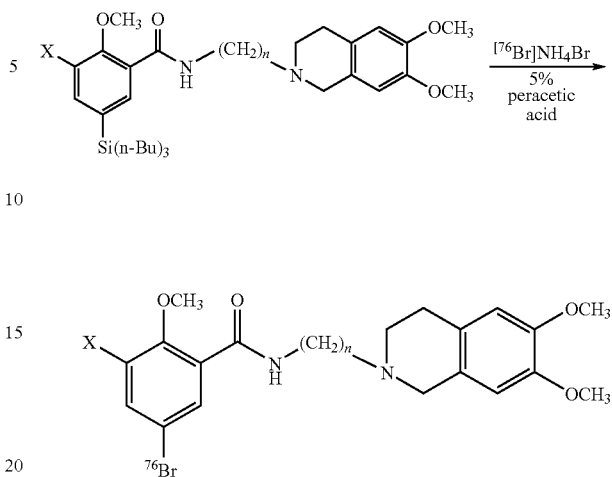

8: X = H, n = 2
6: X = OCH3, n = 4

Scheme II

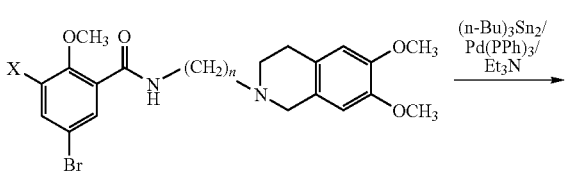

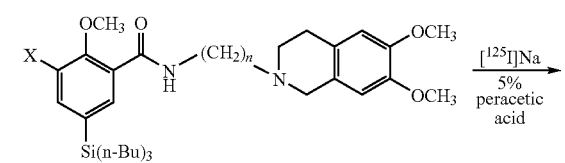

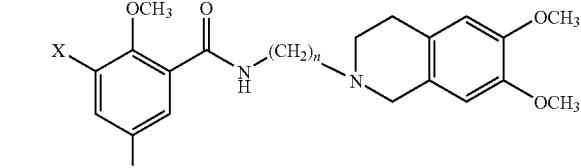

8i: X = H, n = 2
6i: X = OCH3, n = 4

A series of biodistribution studies in tumor-bearing mice were also conducted with [$^{76}$Br]8, [$^{76}$Br]6, [$^{125}$I]8i, and [$^{125}$I]6i. The results of these studies are presented in Tables VI-IX.

TABLE VI

[$^{76}$Br]8 Biodistribution in EMT-6 BALB/C mice

|  | 5 min. | 30 min. | 1 hour | 2 hour |
|---|---|---|---|---|
| % ID per gram | | | | |
| blood | 4.55 ± 0.59 | 2.55 ± 0.06 | 2.08 ± 0.69 | 3.46 ± 0.66 |
| lung | 5.52 ± 0.73 | 1.59 ± 0.10 | 1.20 ± 0.27 | 1.75 ± 0.20 |
| liver(all) | 17.85 ± 3.17 | 5.57 ± 1.31 | 3.09 ± 0.48 | 3.77 ± 0.80 |
| spleen | 3.22 ± 0.75 | 0.92 ± 0.26 | 0.59 ± 0.06 | 0.72 ± 0.05 |
| kidney | 50.08 ± 2.09 | 32.24 ± 4.64 | 15.60 ± 2.01 | 3.61 ± 0.52 |
| muscle | 1.42 ± 0.05 | 0.57 ± 0.07 | 0.56 ± 0.26 | 0.45 ± 0.02 |
| fat | 2.61 ± 0.45 | 0.80 ± 0.05 | 0.66 ± 0.11 | 0.69 ± 0.18 |
| heart | 2.44 ± 0.43 | 0.99 ± 0.13 | 0.78 ± 0.14 | 1.23 ± 0.18 |
| brain | 1.69 ± 0.18 | 0.24 ± 0.05 | 0.15 ± 0.01 | 0.21 ± 0.01 |
| bone | 1.55 ± 0.20 | 0.52 ± 0.02 | 0.50 ± 0.17 | 0.49 ± 0.17 |
| tumor | 2.28 ± 0.14 | 1.30 ± 0.08 | 1.12 ± 0.20 | 1.19 ± 0.13 |
| ratio | | | | |
| Tumor:blood | 0.50 ± 0.04 | 0.51 ± 0.02 | 0.58 ± 0.22 | 0.35 ± 0.21 |
| Tumor:lung | 0.42 ± 0.05 | 0.82 ± 0.05 | 0.98 ± 0.34 | 0.68 ± 0.10 |
| Tumor:muscle | 1.61 ± 0.05 | 2.31 ± 0.40 | 2.47 ± 1.53 | 2.63 ± 2.47 |
| Tumor:fat | 0.90 ± 0.20 | 1.63 ± 0.02 | 1.71 ± 0.29 | 1.82 ± 2.22 |
| Tumor:heart | 0.95 ± 0.13 | 1.32 ± 0.19 | 1.50 ± 0.49 | 0.98 ± 0.13 |

TABLE VII

[$^{76}$Br]6 Biodistribution in EMT-6 BALB/C mice

| % ID per gram | 5 min. | 30 min. | 1 hour | 2 hour | 4 hour |
|---|---|---|---|---|---|
| blood | 2.12 ± 0.20 | 2.20 ± 0.24 | 1.60 ± 0.22 | 0.46 ± 0.07 | 0.21 ± 0.03 |
| lung | 24.64 ± 2.74 | 5.81 ± 1.12 | 2.45 ± 0.17 | 0.74 ± 0.04 | 0.29 ± 0.03 |
| liver(all) | 10.99 ± 0.29 | 8.85 ± 0.52 | 4.58 ± 0.36 | 1.67 ± 0.10 | 0.71 ± 0.08 |
| spleen | 12.50 ± 1.46 | 6.91 ± 1.22 | 2.61 ± 0.62 | 0.60 ± 0.03 | 0.20 ± 0.03 |
| kidney | 31.20 ± 2.92 | 18.51 ± 2.66 | 10.81 ± 1.72 | 1.85 ± 0.54 | 0.57 ± 0.12 |
| muscle | 3.62 ± 0.27 | 1.54 ± 0.49 | 0.61 ± 0.11 | 0.20 ± 0.03 | 0.07 ± 0.01 |
| fat | 3.78 ± 0.97 | 2.27 ± 0.16 | 0.81 ± 0.16 | 0.22 ± 0.05 | 0.04 ± 0.02 |
| heart | 7.31 ± 0.70 | 2.15 ± 0.30 | 1.08 ± 0.07 | 0.30 ± 0.03 | 0.11 ± 0.02 |
| brain | 1.60 ± 0.15 | 0.41 ± 0.06 | 0.17 ± 0.02 | 0.05 ± 0.00 | 0.03 ± 0.00 |
| bone | 3.10 ± 0.67 | 2.76 ± 0.58 | 1.38 ± 0.09 | 0.56 ± 0.20 | 0.12 ± 0.03 |
| tumor | 4.78 ± 0.78 | 5.31 ± 0.62 | 3.98 ± 0.58 | 1.71 ± 0.17 | 0.68 ± 0.15 |
| ratio | | | | | |
| Tumor:blood | 2.25 ± 0.28 | 2.41 ± 0.08 | 2.53 ± 0.54 | 3.79 ± 0.99 | 3.17 ± 0.58 |
| Tumor:lung | 0.19 ± 0.02 | 0.93 ± 0.09 | 1.64 ± 0.30 | 2.30 ± 0.13 | 2.36 ± 0.46 |
| Tumor:muscle | 1.32 ± 0.16 | 3.70 ± 1.06 | 6.76 ± 2.09 | 8.81 ± 0.91 | 9.48 ± 2.14 |
| Tumor:fat | 1.30 ± 0.24 | 2.35 ± 0.34 | 5.09 ± 1.39 | 7.97 ± 1.95 | 20.69 ± 10.77 |
| Tumor:heart | 0.65 ± 0.07 | 2.48 ± 0.17 | 3.72 ± 0.72 | 5.77 ± 0.60 | 6.24 ± 1.28 |

TABLE VIII

[$^{125}$I]8i Biodistribution in EMT-6 BALB/C mice

|  | 5 min. | 30 min. | 1 hour | 2 hour |
|---|---|---|---|---|
| % ID per gram | | | | |
| blood | 6.90 ± 1.29 | 2.44 ± 0.65 | 1.17 ± 0.29 | 3.37 ± 1.23 |
| lung | 5.95 ± 1.30 | 1.39 ± 0.29 | 0.81 ± 0.20 | 1.27 ± 0.37 |
| liver(all) | 41.37 ± 7.23 | 8.20 ± 1.05 | 2.87 ± 0.34 | 3.47 ± 1.05 |
| kidney | 54.77 ± 8.42 | 38.59 ± 2.05 | 18.07 ± 2.07 | 8.46 ± 1.26 |
| muscle | 1.47 ± 0.20 | 0.70 ± 0.25 | 0.37 ± 0.23 | 0.38 ± 0.06 |
| fat | 3.46 ± 0.59 | 1.03 ± 0.44 | 0.77 ± 0.66 | 0.37 ± 0.13 |
| heart | 2.79 ± 0.35 | 0.94 ± 0.19 | 0.40 ± 0.02 | 0.86 ± 0.26 |
| brain | 1.42 ± 0.33 | 0.20 ± 0.06 | 0.06 ± 0.02 | 0.09 ± 0.03 |
| tumor | 2.91 ± 0.40 | 1.33 ± 0.13 | 0.71 ± 0.12 | 0.82 ± 0.09 |
| ratio | | | | |
| Tumor:blood | 0.42 ± 0.03 | 0.57 ± 0.12 | 0.62 ± 0.09 | 0.26 ± 0.08 |
| Tumor:lung | 0.50 ± 0.07 | 0.98 ± 0.16 | 0.91 ± 0.24 | 0.67 ± 0.14 |
| Tumor:muscle | 2.00 ± 0.37 | 2.06 ± 0.69 | 2.14 ± 0.99 | 2.17 ± 0.23 |
| Tumor:fat | 0.84 ± 0.06 | 1.49 ± 0.65 | 1.93 ± 1.87 | 2.44 ± 0.77 |
| Tumor:heart | 1.04 ± 0.08 | 1.44 ± 0.18 | 1.81 ± 0.32 | 1.00 ± 0.27 |

TABLE IX

[$^{125}$I]6i Biodistribution in EMT-6 BALB/C mice

| % ID per gram | 5 min. | 30 min. | 1 hour | 2 hour | 4 hour |
|---|---|---|---|---|---|
| blood | 2.37 ± 0.26 | 2.19 ± 0.16 | 1.52 ± 0.49 | 0.65 ± 0.07 | 0.29 ± 0.11 |
| lung | 27.13 ± 1.61 | 5.50 ± 0.62 | 2.12 ± 0.19 | 1.01 ± 0.18 | 0.29 ± 0.05 |
| liver(all) | 13.20 ± 2.04 | 8.77 ± 0.88 | 4.24 ± 0.60 | 1.91 ± 0.20 | 0.90 ± 0.21 |
| kidney | 29.51 ± 2.23 | 13.69 ± 0.35 | 5.94 ± 1.22 | 2.45 ± 0.25 | 0.63 ± 0.11 |
| muscle | 4.10 ± 0.33 | 1.21 ± 0.17 | 0.87 ± 0.22 | 0.31 ± 0.10 | 0.10 ± 0.04 |
| fat | 4.15 ± 0.91 | 1.73 ± 0.20 | 0.74 ± 0.17 | 0.33 ± 0.08 | 0.10 ± 0.05 |
| heart | 6.55 ± 0.54 | 1.94 ± 0.09 | 0.91 ± 0.10 | 0.40 ± 0.05 | 0.15 ± 0.04 |
| brain | 1.53 ± 0.14 | 0.39 ± 0.03 | 0.15 ± 0.03 | 0.06 ± 0.01 | 0.02 ± 0.01 |
| tumor | 4.02 ± 0.55 | 4.50 ± 0.43 | 3.53 ± 0.42 | 1.88 ± 0.76 | 0.82 ± 0.09 |
| ratio | | | | | |
| Tumor:blood | 1.73 ± 0.46 | 2.07 ± 0.32 | 2.44 ± 0.53 | 2.83 ± 1.62 | 3.11 ± 0.85 |
| Tumor:lung | 0.15 ± 0.02 | 0.82 ± 0.09 | 1.66 ± 0.17 | 1.99 ± 1.04 | 2.83 ± 0.19 |
| Tumor:muscle | 0.98 ± 0.13 | 3.94 ± 0.55 | 4.26 ± 0.74 | 6.99 ± 4.44 | 8.98 ± 3.01 |
| Tumor:fat | 1.00 ± 0.20 | 2.62 ± 0.27 | 4.85 ± 0.67 | 5.86 ± 2.93 | 9.59 ± 4.55 |
| Tumor:heart | 0.61 ± 0.07 | 2.32 ± 0.18 | 3.89 ± 0.08 | 4.85 ± 2.31 | 5.91 ± 1.65 |

Blocking studies. The results of the above biodistribution studies in tumor bearing rodents (mice) showed the utility that [$^{11}$C]10, [$^{76}$Br]6, and [$^{125}$I]6i as potential candidates for further evaluation.

The inventors then conducted blocking studies in order to confirm that the radiotracer labeled $\sigma_2$ receptors in the breast tumors. These studies were conducted using the nonselective sigma ligand, YUN 143 (1 mg/kg, i.v.), which has a high affinity for both $\sigma_1$ and $\sigma_2$ receptors. We have previously reported that [$^{18}$F]YUN 143 labels $\sigma_1$ and $\sigma_2$ receptors in breast tumor xenografts (Mach et al., 2001). The results of our blocking study are shown in FIG. 2 and are consistent with the labeling of $\sigma_2$ receptors in vivo.

Comparison with [$^{18}$F]FLT. One of the specific aims of the project was to compare the $\sigma_2$ receptor imaging approach with the nucleoside analog, [$^{18}$F]FLT. These studies were conducted and the results are summarized in FIGS. 3-5. In this study, the uptake of [$^{18}$F]FLT at 1 hr was compared with the one hr data for [$^{11}$C]Compound 10. For studies comparing [$^{18}$F]FLT with [$^{76}$Br]6 and [$^{125}$I]6i, the two hr post-i.v. injection time point was used.

MicroPET® Imaging Studies—The inventors conducted microPET® imaging studies with [$^{76}$Br]6 in Balb-c mice bearing EMT-6 breast tumor xenografts to model a living mammal afflicted with cancer. The results of the imaging studies are shown in FIG. 6. Note the high uptake of the radiotracer in the NCA study (left image), which can be blocked with a known sigma receptor ligand (right image). These data show that [$^{76}$Br] Compound 6 is a potential radiotracer for imaging the $\sigma_2$ receptor status of breast tumors.

Log P Calculations. The lipophilicity of each compound was calculated using the program Clog P (Advanced Chemistry Development, Inc.; Toronto, Canada). The results of the log P calculations are shown in Table X. The log P values ranged from 2.31 to 3.43.

TABLE X

| # | Log P |
|---|---|
| 9 | 2.31 |
| 10 | 2.84 |
| 8 | 3.17 |
| 7 | 3.33 |

TABLE X-continued

| # | Log P |
|---|---|
| 6 | 3.43 |
| 6i | 3.24 |

The relationship between the uptake of the radiolabeled benzamide analogs (% I.D. at 5 min post-i.v. injection) and log P is shown in Figure X. There was no clear trend with respect to log P and tumor uptake (top graph) and tumor:fat ratio (bottom graph). The higher tumor:fat ratio of [$^{76}$Br]6 and [$^{125}$I]6i was due to the later time point that can be imaged because of the longer half-life of Br-76 and I-125 versus that of C-11.

The inventors identified a $\sigma_2$ receptor imaging agent that has in vivo properties equal to or greater than that of [$^{18}$F]FLT. Based on the data described above we have identified three $\sigma_2$ radiotracers:

1. [$^{11}$C]10, which has tumor:lung and tumor:fat ratios equal to [$^{18}$F]FLT and tumor:blood, tumor:muscle and tumor:heart ratios that are greater than that of [$^{18}$F]FLT;

2. [$^{76}$Br]6, which has higher tumor:background ratios greater than that observed with [$^{18}$F]FLT;

3. [$^{125}$I]6i, which has a similar tumor:fat ratio as [$^{18}$F]FLT and exceeds [$^{18}$F]FLT in all other tumor:background ratios.

We have specifically identified two potential PET radiotracers ([$^{11}$C]10 and [$^{76}$Br]6) and one SPECT radiotracer ($^{123}$I]6i) for imaging the $\sigma_2$ receptor status of breast tumors. In addition, 6i can also be labeled with $^{124}$I, potentially yielding another PET radiotracer for imaging $\sigma_2$ receptors in breast tumors.

In conclusion, the inventors have identified and successfully prepared three radiotracers that are either equal to or greater than [$^{18}$F]FLT in a living rodent model of breast tumor.

REFERENCES

Mach R H, Smith C R, Al-Nabulsi I, Whirrett B R, Childers S R, Wheeler K T. Sigma-2 receptors as potential biomarkers of profileration in breast cancer. Cancer Res 1997; 57:156-161.

Al-Nabulsi I, Mach R H, Wang L-M, Wallen C A, Keng P C, Sten K, Childers S R, Wheeler K T. Effect of ploidy, recruitment, environmental factors, and tamoxifen treatment on the expression of sigma-2 receptors in proliferating and quiescent tumor cells. Br J Cancer 1999; 81:925-933.

Wheeler K T, Wang L-M, Wallen C A, Childers S R, Cline J M, Keng P C, Mach R H. Sigma-2 receptors as a biomarker of proliferation in solid tumors. Br J Cancer 2000; 86:1223-1232.

Mach R H, Huang Y, Buchheimer N, Kuhner R, Wu L, Morton T E, Wang L-M, Ehrenkaufer R L, Wallen C A, Wheeler K T. [$^{18}$F]N-4'-fluorobenzy-1-4-(3-bromophenyl)acetamide for imaging the sigma receptor status of shown tumors: comparison with [$^{18}$F]FDG and [$^{125}$I]IUDR. Nucl Med Biol 2001; 28:451-458.

While the invention has been described in terms of various specific embodiments, those skilled in the art will recognize that the invention can be practiced with modification within the spirit and scope of the claims.

What is claimed is:

1. A method of detecting a cancer in a mammal in vivo, the method comprising:
   a) administering to a mammal a radiolabeled compound or salt thereof of Formula

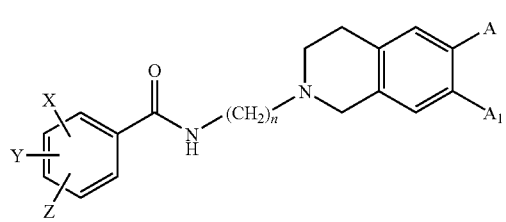

wherein:
   each of X, Y, and Z is a substituent selected from the group consisting of a hydrogen, a halogen, a $C_1$-$C_4$ alkoxyl, a $C_1$-$C_4$ alkyl, a $C_1$-$C_4$ fluoroalkyl, a $C_1$-$C_4$ fluoroalkoxyl, a $CF_3$, and an $OCF_3$, wherein at least one of X, Y and Z comprises a radioisotope selected from the group consisting of a bromine, an iodine, a carbon of a 2-methoxyl and a tritium of a 2-methoxyl;
   n is an integer from 2 to about 10; and
   each of A and $A_1$ is independently selected from the group consisting of a $C_1$-$C_4$ alkoxyl, a $C_1$-$C_4$ fluoroalkyl and a $C_1$-$C_4$ fluoroalkoxyl; and
   b) detecting the distribution of the radioisotope in the mammal, whereby a cell having a high density of the radioisotope compared to quiescent cells is diagnostic for a cancerous tumor cell.

2. A method of detecting a cancer in accordance with claim 1, wherein the radioisotope is a $^3$H.

3. A method of detecting a cancer in accordance with claim 1, wherein the radioisotope is a $^{11}$C.

4. A method of detecting a cancer in accordance with claim 1, wherein the compound is selected from the group consisting of:

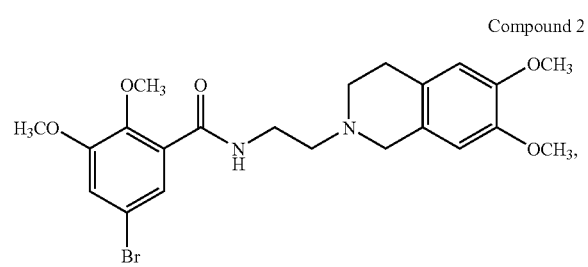

Compound 2

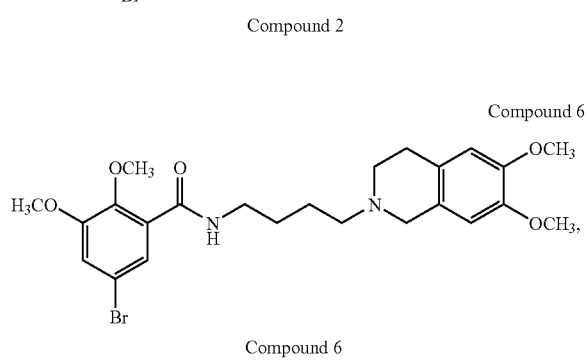

Compound 6

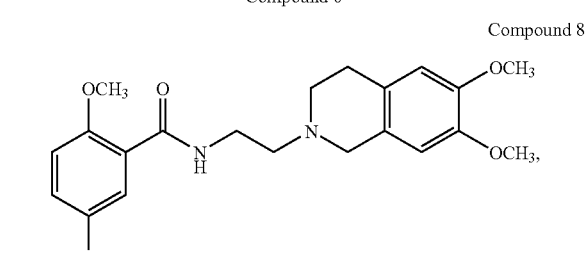

Compound 8

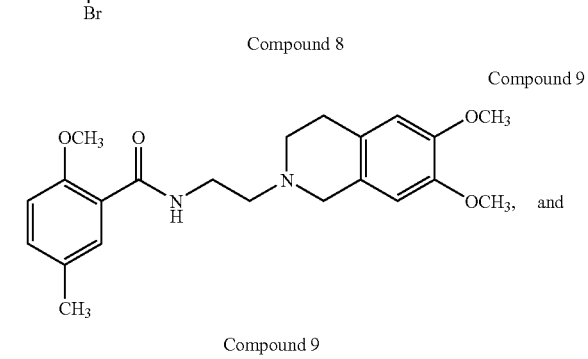

Compound 9

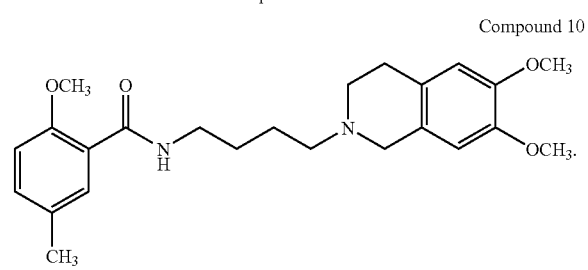

Compound 10

5. A method of detecting a cancer in accordance with claim 1, wherein each of A and $A_1$ is a methoxyl.

6. A method of detecting a cancer in accordance with claim 1, wherein the compound is Compound 6

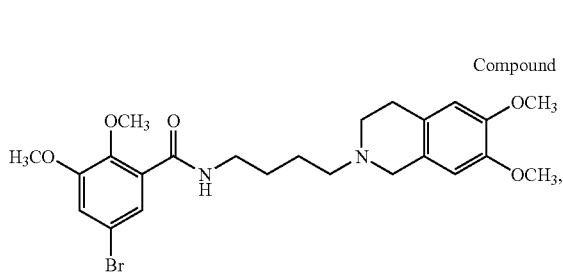

Compound 6 and wherein the Br is a $^{76}$Br.

7. A method of detecting a cancer in accordance with claim 1, wherein the compound is Compound 10

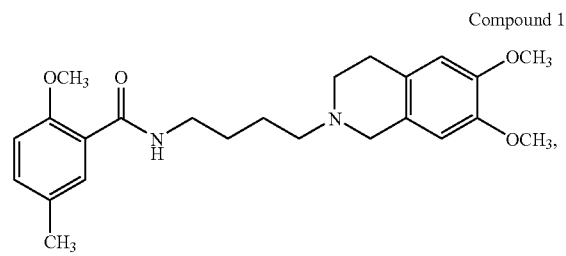

Compound 10 and wherein the 2-methoxyl comprises a $^{11}$C.

8. A method of detecting a cancer in accordance with claim 1, wherein the radioisotope is selected from the group consisting of an $^{123}$I, an $^{124}$I and an $^{125}$I.

9. A method of detecting a cancer in accordance with claim 8, wherein the radioisotope is an $^{123}$I.

10. A method of detecting a cancer in accordance with claim 8, wherein the radioisotope is an $^{125}$I.

11. A method of detecting a cancer in accordance with claim 8, wherein the compound has the structure

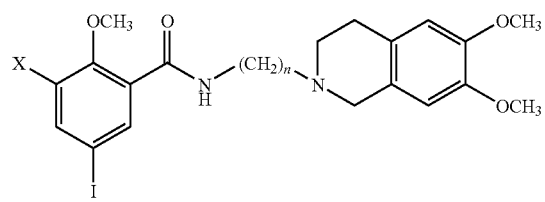

wherein X is H or OCH$_3$ and n=2 or 4.

12. A method of detecting a cancer in accordance with claim 8, wherein the compound is selected from the group consisting of

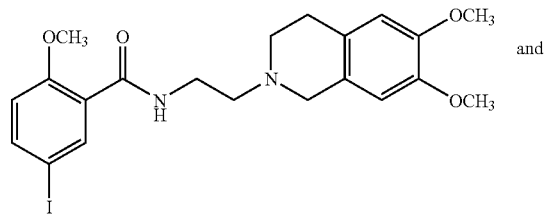

and

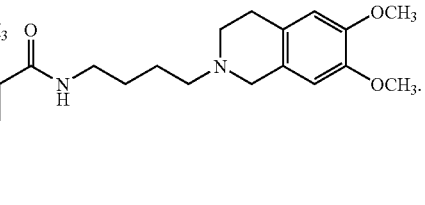

-continued

13. A method of detecting a cancer in accordance with claim 1, wherein the administering to a mammal a radiolabeled compound or salt thereof comprises administering to the mammal a pharmaceutical composition comprising the radiolabeled compound or salt thereof and a pharmaceutically acceptable carrier.

14. A method of detecting a cancer in accordance with claim 1, wherein the detecting the distribution of the radioisotope comprises imaging the distribution of the radioisotope.

15. A method of detecting a cancer in accordance with claim 1, wherein the mammal is a human.

16. A method of determining the proliferative status of cells comprised by a mammalian tumor in vivo, the method comprising:
   a) administering to a mammal comprising a tumor, a radiolabeled compound or salt thereof of Formula

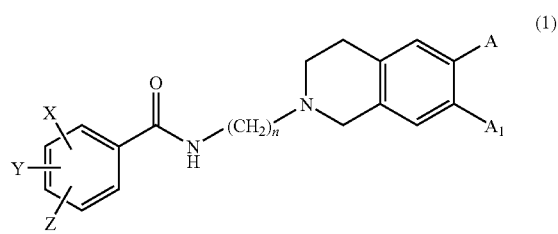

(1)

wherein:
   each of X, Y, and Z is a substituent selected from the group consisting of a hydrogen, a halogen, a $C_1$-$C_4$ alkoxyl, a $C_1$-$C_4$ alkyl, a $C_1$-$C_4$ fluoroalkyl, a $C_1$-$C_4$ fluoroalkoxyl, a $CF_3$, and an $OCF_3$, wherein at least one of X, Y and Z comprises a radioisotope selected from the group consisting of a bromine, an iodine, a carbon of a 2-methoxyl and a tritium of a 2-methoxyl;
   n is an integer from 2 to about 10;
   each of A and $A_1$ is independently selected from the group consisting of a $C_1$-$C_4$ alkoxyl, a $C_1$-$C_4$ fluoroalkyl and a $C_1$-$C_4$ fluoroalkoxyl; and
   b) determining, for cells comprised by the tumor, a ratio of proliferating cells to quiescent cells.

17. A method of determining the proliferative status of cells comprised by a mammalian tumor in vivo in accordance with claim 16, wherein the radioisotope is selected from the group consisting of a $^3$H and a $^{11}$C.

18. A method of determining the proliferative status of cells comprised by a mammalian tumor in vivo in accordance with claim 16, wherein the compound is selected from the group consisting of:

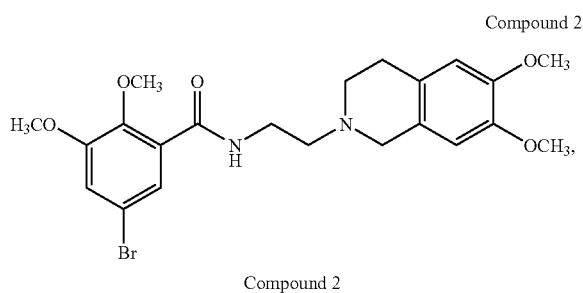

Compound 2

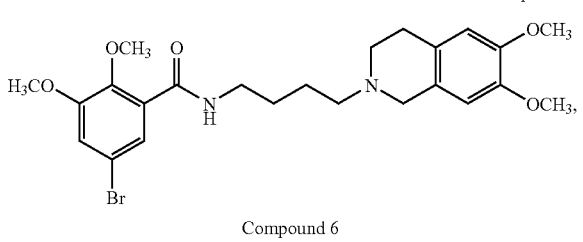

Compound 6

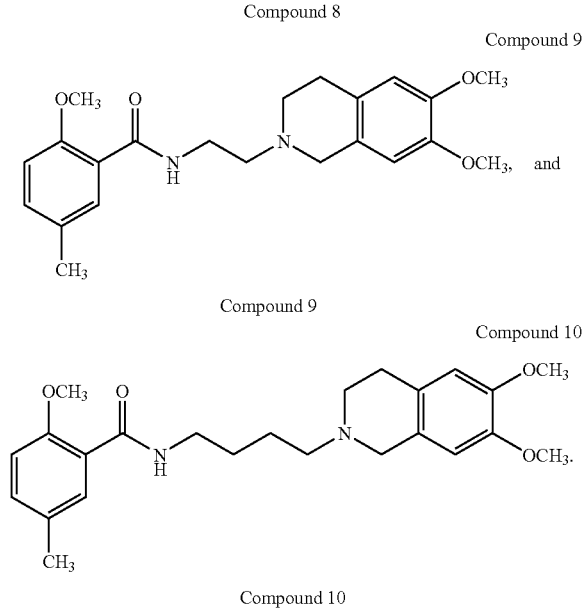

Compound 8

Compound 9

Compound 10

19. A method of determining the proliferative status of cells comprised by a mammalian tumor in vivo in accordance with claim 16, wherein each of A and $A_1$ is a methoxyl.

20. A method of determining the proliferative status of cells comprised by a mammalian tumor in vivo in accordance with claim 16, wherein the compound is Compound 6

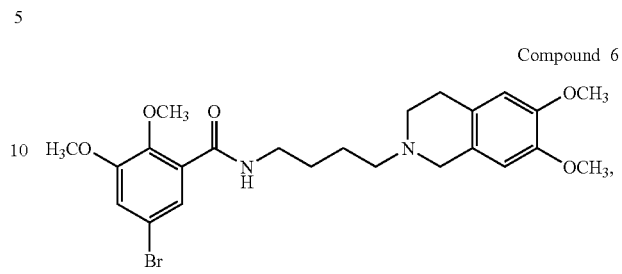

and wherein the Br is a $^{76}$Br.

21. A method of determining the proliferative status of cells comprised by a mammalian tumor in vivo in accordance with claim 16, wherein the compound is Compound 10

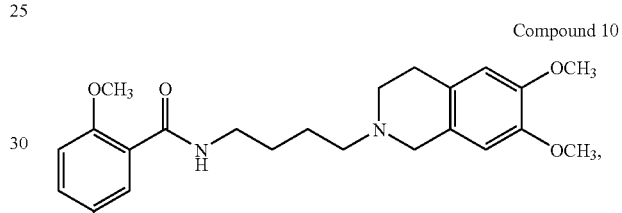

and wherein the 2-methoxyl comprises a $^{11}$C.

22. A method of determining the proliferative status of cells comprised by a mammalian tumor in vivo in accordance with claim 16, wherein the radioisotope is selected from the group consisting of an $^{123}$I, an $^{124}$I and an $^{125}$I.

23. A method of determining the proliferative status of cells comprised by a mammalian tumor in vivo in accordance with claim 22, wherein the radioisotope is selected from the group consisting of an $^{123}$I and an $^{121}$I.

24. A method of determining the proliferative status of cells comprised by a mammalian tumor in vivo in accordance with claim 22, wherein the compound has the structure

wherein X is H or $OCH_3$ and n=2 or 4.

25. A method of determining the proliferative status of cells comprised by a mammalian tumor in vivo in accordance with claim 22, wherein the compound is selected from the group consisting of

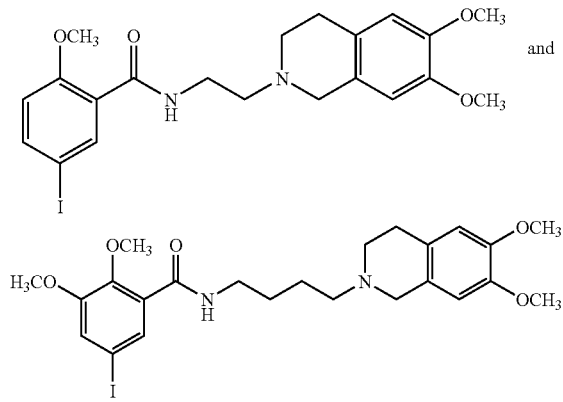

26. A method of determining the proliferative status of cells comprised by a mammalian tumor in vivo in accordance with claim 16, wherein the administering to a mammal a radiolabeled compound or salt thereof comprises administering to the mammal a pharmaceutical composition comprising the radiolabeled compound or salt thereof and a pharmaceutically acceptable carrier.

27. A method of determining the proliferative status of cells comprised by a mammalian tumor in vivo in accordance with claim 16, wherein the mammal is a human.

28. A method of determining progression of a cancerous tumor in a mammal, the method comprising:

a) administering to a mammal a radiolabeled compound or salt thereof of Formula

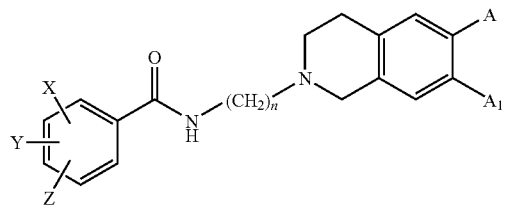

(1)

wherein:
each of X, Y, and Z is a substituent selected from the group consisting of a hydrogen, a halogen, a $C_1$-$C_4$ alkoxyl, a $C_1$-$C_4$ alkyl, a $C_1$-$C_4$ fluoroalkyl, a $C_1$-$C_4$ fluoroalkoxyl, a $CF_3$, and an $OCF_3$, wherein at least one of X, Y and Z comprises a radioisotope selected from the group consisting of a bromine, an iodine, a carbon of a 2-methoxyl and a tritium of a 2-methoxyl;
n is an integer from 2 to about 10; and
each of A and $A_1$ is independently selected from the group consisting of a $C_1$-$C_4$ alkoxyl, a $C_1$-$C_4$ fluoroalkyl and a $C_1$-$C_4$ fluoroalkoxyl; and b) acquiring, at a first selected time, a first image of the distribution of the radioisotope in the mammal;
c) acquiring, at a second selected time, a second image of the distribution of the radioisotope in the mammal, whereby the radioisotope accumulates at a tumor, and a change in intensity of the radioisotope at the tumor from the first selected time to the second selected time indicates a change in tumor size.

29. A method of determining progression of a cancerous tumor in accordance with claim 28, wherein the radioisotope is selected from the group consisting of a $^3H$ and a $^{11}C$.

30. A method of determining progression of a cancerous tumor in accordance with claim 28, wherein the compound is selected from the group consisting of:

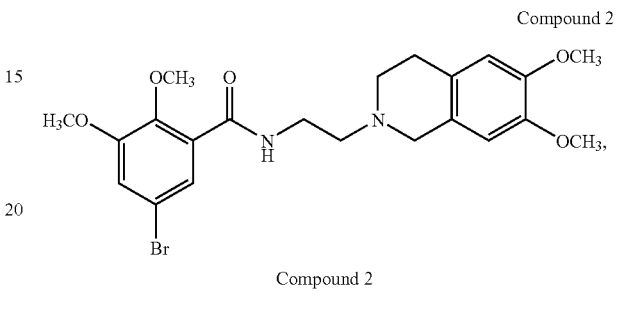

Compound 2

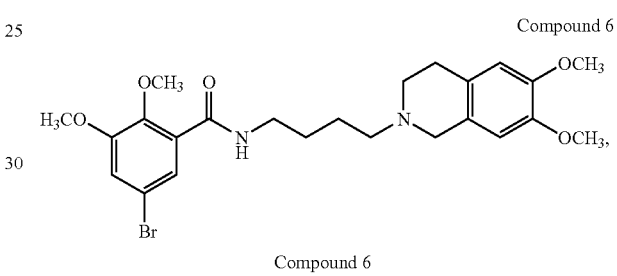

Compound 6

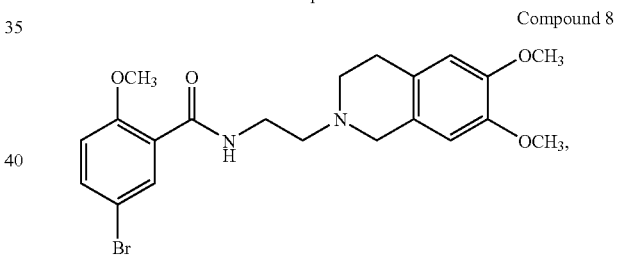

Compound 8

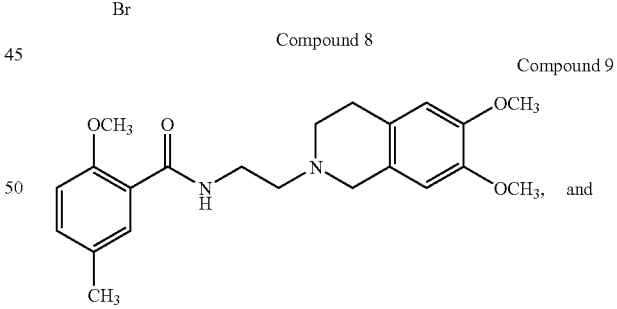

Compound 9

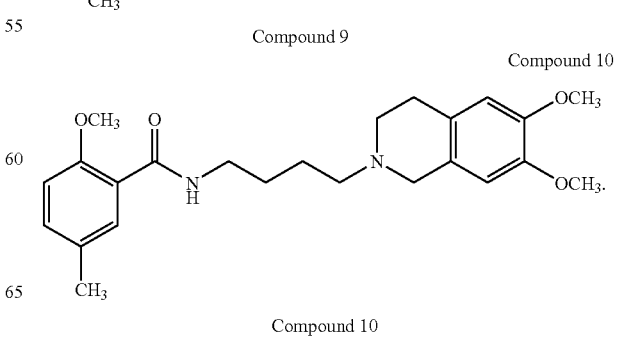

Compound 10

31. A method of determining progression of a cancerous tumor in accordance with claim 28, wherein each of A and $A_1$ is a methoxyl.

32. A method of determining progression of a cancerous tumor in accordance with claim 28, wherein the compound is Compound 6

Compound 6

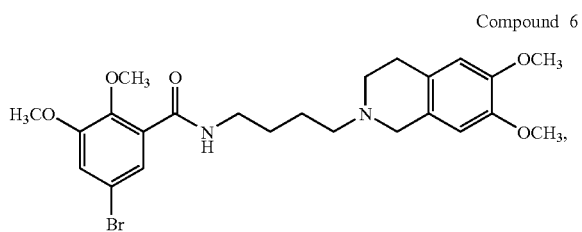

and wherein the Br is a $^{76}$Br.

33. A method of determining progression of a cancerous tumor in accordance with claim 28, wherein the compound is Compound 10

Compound 10

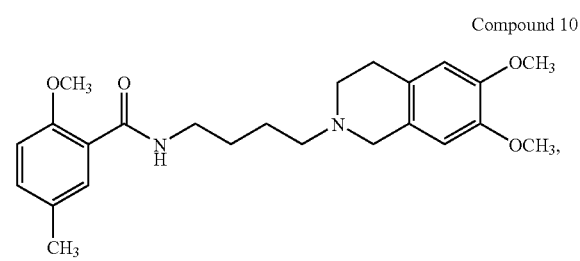

and wherein the 2-methoxyl comprises a $^{11}$C.

34. A method of determining progression of a cancerous tumor in accordance with claim 28, wherein the radioisotope is selected from the group consisting of an $^{123}$I, an $^{124}$I and an $^{125}$I.

35. A method of determining progression of a cancerous tumor in accordance with claim 34, wherein the radioisotope is selected from the group consisting of an $^{123}$I and an $^{125}$I.

36. A method of determining progression of a cancerous tumor in accordance with claim 34, wherein the compound has the structure

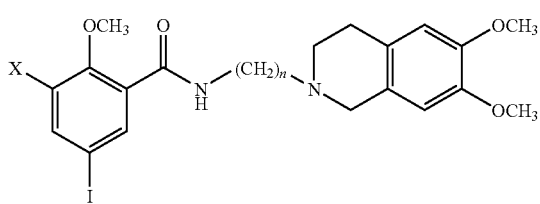

wherein X is H or $OCH_3$ and n=2 or 4.

37. A method of determining progression of a cancerous tumor in accordance with claim 34, wherein the compound is selected from the group consisting of

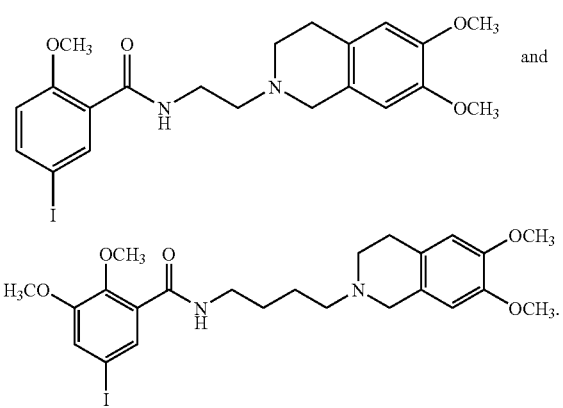

38. A method of determining progression of a cancerous tumor in accordance with claim 28, wherein the administering to a mammal a radiolabeled compound or salt thereof comprises administering to the mammal a pharmaceutical composition comprising the radiolabeled compound or salt thereof and a pharmaceutically acceptable carrier.

39. A method of determining progression of a cancerous tumor in accordance with claim 28, wherein the mammal is a human.

* * * * *